United States Patent
Muro et al.

(10) Patent No.: US 10,394,626 B2
(45) Date of Patent: Aug. 27, 2019

(54) EVENT FLOW SYSTEM AND EVENT FLOW CONTROL METHOD

(71) Applicant: HITACHI, LTD., Tokyo (JP)

(72) Inventors: Keiro Muro, Tokyo (JP); Hiromitsu Nakagawa, Tokyo (JP)

(73) Assignee: HITACHI, LTD., Tokyo (JP)

( * ) Notice: Subject to any disclaimer, the term of this patent is extended or adjusted under 35 U.S.C. 154(b) by 0 days.

(21) Appl. No.: 15/816,366

(22) Filed: Nov. 17, 2017

(65) Prior Publication Data
US 2018/0173576 A1      Jun. 21, 2018

(30) Foreign Application Priority Data

Dec. 19, 2016   (JP) ................. 2016-245124

(51) Int. Cl.
| | |
|---|---|
| G06F 3/00 | (2006.01) |
| G06F 9/44 | (2018.01) |
| G06F 9/46 | (2006.01) |
| G06F 13/00 | (2006.01) |
| G06F 9/54 | (2006.01) |
| G05B 15/02 | (2006.01) |
| G01N 29/44 | (2006.01) |
| G01N 29/14 | (2006.01) |

(52) U.S. Cl.
CPC ............ *G06F 9/542* (2013.01); *G01N 29/14* (2013.01); *G01N 29/4454* (2013.01); *G05B 15/02* (2013.01)

(58) Field of Classification Search
CPC ....................................................... G06F 9/542
USPC ....................................................... 719/318
See application file for complete search history.

(56) References Cited

U.S. PATENT DOCUMENTS

2013/0042011 A1* 2/2013 Sugizaki .............. H04Q 3/0045
                                                              709/227

FOREIGN PATENT DOCUMENTS

JP         2007-249978 A       9/2007

* cited by examiner

*Primary Examiner* — Timothy A Mudrick
(74) *Attorney, Agent, or Firm* — Volpe and Koenig, P.C.

(57) ABSTRACT

An event flow system connecting nodes, for which processes are defined, from an upstream side to a downstream side by an event which is generated due to a certain process and is used by another process to realize a process flow is provided. The event flow system includes: a process flow builder configured to build a process flow using a plurality of nodes, one or more events, and a reverse event that sends a predetermined request, from a downstream node to an upstream node disposed further toward an upstream side than the downstream node; and a process flow executer configured to execute a process defined for each of the plurality of nodes according to the event and the reverse event.

9 Claims, 37 Drawing Sheets

FIG. 7

Node Table ~D4

| Class | IN port number | OUT port number | Cost |
|---|---|---|---|
| ClassI | 0 | 1 | 10 |
| ClassA | 1 | 2 | 10 |
| ClassB | 1 | 1 | 10 |
| ClassC | 1 | 1 | 10 |
| ClassD | 1 | 1 | 10 |
| ClassE | 2 | 1 | 10 |
| ClassO | 1 | 0 | 10 |

Flow Table

| Node | Class  | I0    | I1         | ... I-n | O0    | O1         | ... O-n | Cost |
|------|--------|-------|------------|---------|-------|------------|---------|------|
| I    | ClassI | -     | -          | -       | A#I0  | -          | -       | 11   |
| A    | ClassA | I#O0  | -          | -       | B#I0  | C#I0,D#I0  | -       | 8    |
| B    | ClassB | A#O0  | -          | -       | E#I0  | E#I0       | -       | 7    |
| C    | ClassC | A#O1  | -          | -       | E#I1  | E#I1       | -       | 12   |
| D    | ClassD | A#O1  | -          | -       | E#I1  | E#I1       | -       | 13   |
| E    | ClassE | B#O0  | C#O0,D#O0  | -       | O#I0  | -          | -       | 14   |
| O    | ClassO | E#O0  | -          | -       | -     | -          | -       | 11   |

FIG. 11

Event Queue ~D1

| FROM | TO | EVENT | Limit |
|---|---|---|---|
| I#O0 | A#I0 | e1 | 10 |
| A#O0 | B#I0 | e2 | 10 |
| A#O0 | B#I0 | e3 | 10 |
| E#O0 | O#I0 | e4 | 10 |

FIG. 12

Reverse Queue ~D2

| FROM | TO   | EVENT | Limit |
|------|------|-------|-------|
| O#I0 | E#O0 | r1    | 10    |
| E#I0 | B#O0 | r2    | 10    |
| B#I0 | A#O0 | r3    | 10    |

FIG. 13
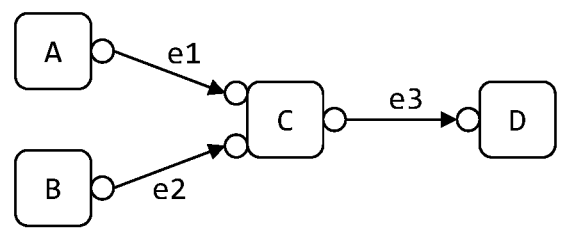
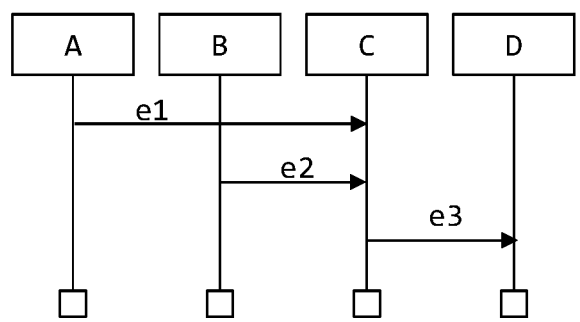

FIG. 14
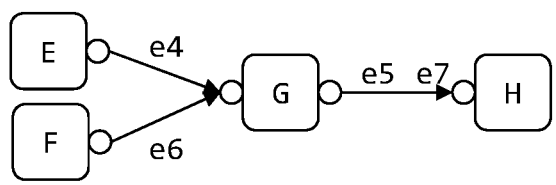
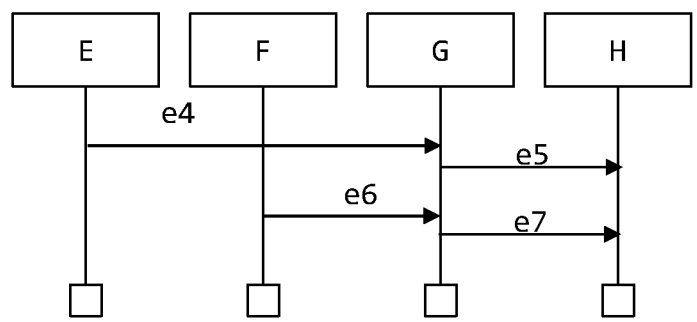

(a) Transaction

(b) Filter

(c) Switcher

EVENT FLOW SYSTEM AND EVENT FLOW CONTROL METHOD

BACKGROUND

The present invention relates to a system that builds and executes a process flow for events.

An abnormality monitoring system that detects occurrence of an abnormality in a target system analyzes data published from a number of sensors installed in the site of the target system according to predetermined analysis logics to discover an abnormality, estimate the cause of the abnormality, and assess the risk of the abnormality. In an abnormality monitoring system of this type, desired conditions can be set for abnormality monitoring by applying a plurality of analysis logics in stages. An example of a process flow executed in stages will be described.

For example, an edge node configured by a small machine installed in the site of a wind power generation system calculates 10 minutes of statistics from the amount of vibration measured by sensors installed in windmills and sends the calculated statistics to a datacenter every 10 minutes as 10-minute statistical information. The datacenter analyzes the 10-minute statistical information, and upon detecting an abnormality in a certain windmill, analyzes a vibration measured by a sensor installed in another position of the windmill in the same time and the picture of the windmill and the surroundings thereof captured by a camera to estimate the cause of the abnormality. Moreover, when a certain abnormality is detected from the 10-minute statistical information, the datacenter executes a number of vibration simulations on a windmill tower to assess the risk of damage to the tower and blades.

A software engine that builds and executes such a series of process flows is known. A software engine of this type which employs an event-driven architecture that defines a process flow using nodes and an event flow is known. In the event-driven architecture, since an upstream node of the event flow can operate regardless of a configuration and a process of a downstream node, it is easy to build the process flow.

However, in an event-driven architecture, an upstream node executes a predetermined process and outputs processing result data regardless of whether the process is used by a downstream node. Due to this, a useless process of allowing an upstream node to generate and send data which is not actually used by a downstream node is performed. For example, although a time in which an abnormality is detected is extremely shorter than a time in which an abnormality is not detected, if a process for estimating the cause of an abnormality is executed continuously in a time in which an abnormality is not detected, the process is a useless process.

In contrast, Japanese Patent Application Publication No. 2007-249978 discloses a technique of reducing a waste of processing. In a parallel simulation, when processing is settled because a response is already discovered halfway parallel processing, subsequent redundant tasks are cancelled and processing is reduced.

SUMMARY

However, since the technique disclosed in Japanese Patent Application Publication No. 2007-249978 is a technique of cancelling tasks when settling processing, the technique is not suitable for reducing such a useless process of generating data which is not used on the downstream as described above.

A process flow building method of explicitly describing which process will be executed when a certain condition is established using a command-driven flow is known. However, in a process flow building method of this type, a conditional branching process other than an original analysis flow becomes complex and a maintenance performance deteriorates.

An object of the present invention is to provide a technique capable of building a process flow in a simple configuration and reducing execution of useless processes included in the process flow.

An event flow system according to an embodiment of the present invention is an event flow system that connects nodes, for which processes are defined, from an upstream side to a downstream side by an event which is generated due to a certain process and is used by another process to realize a process flow, the event flow system including: a process flow builder that builds a process flow using a plurality of nodes, one or more events, and a reverse event that sends a predetermined request from a downstream node to an upstream node disposed further toward an upstream side than the downstream node; and a process flow executer that executes a process defined for each of the plurality of nodes according to the event and the reverse event.

According to the present invention, since it is possible to send a request from a downstream node to an upstream node using a reverse event, it is possible to change the operation of the upstream node to reduce a useless process on the basis of the state of the downstream node. Therefore, it is possible to build a process flow without using a complex conditional branching logic and to reduce a useless process in execution of the process flow.

BRIEF DESCRIPTION OF THE DRAWINGS

FIG. 7 is a table illustrating an example of a node table corresponding to the process flow illustrated in FIG. 6;

FIG. 8 is a table illustrating an example of a flow table corresponding to the process flow illustrated in FIG. 6;

FIG. 11 is a table illustrating an example of an event queue corresponding to an execution state of the process flow illustrated in FIG. 10;

FIG. 12 is a table illustrating an example of a reverse event queue corresponding to an execution state of the process flow illustrated in FIG. 10;

FIG. 13 is a sequence diagram illustrating an example of a state in which an event flows between nodes by execution of a process flow;

FIG. 14 is a sequence diagram illustrating another example of a state in which an event flows between nodes by execution of a process flow;

DETAILED DESCRIPTION OF THE EMBODIMENT

Hereinafter, an embodiment of the present invention will be described with reference to the drawings.

Figure 1:
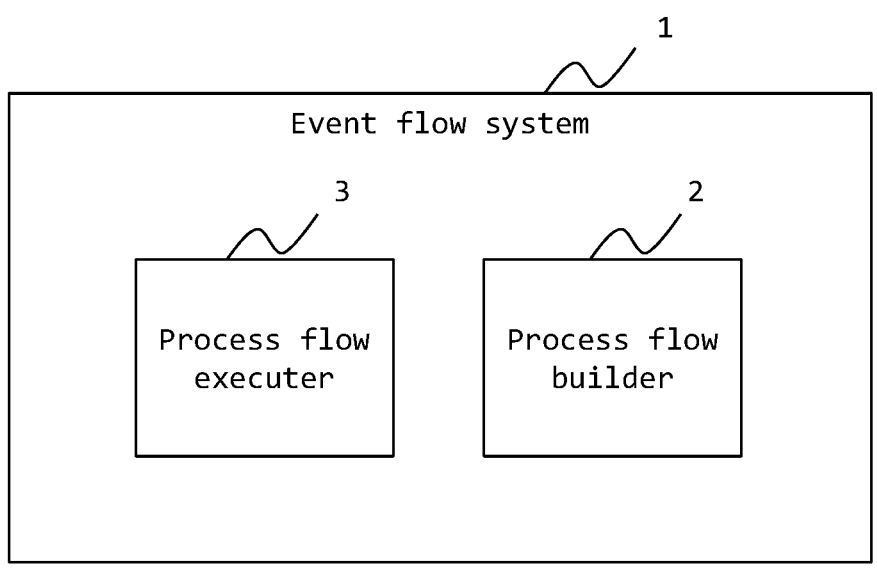
FIG. 1 is a schematic block diagram of an event flow system according to the present embodiment.
Figure 2:
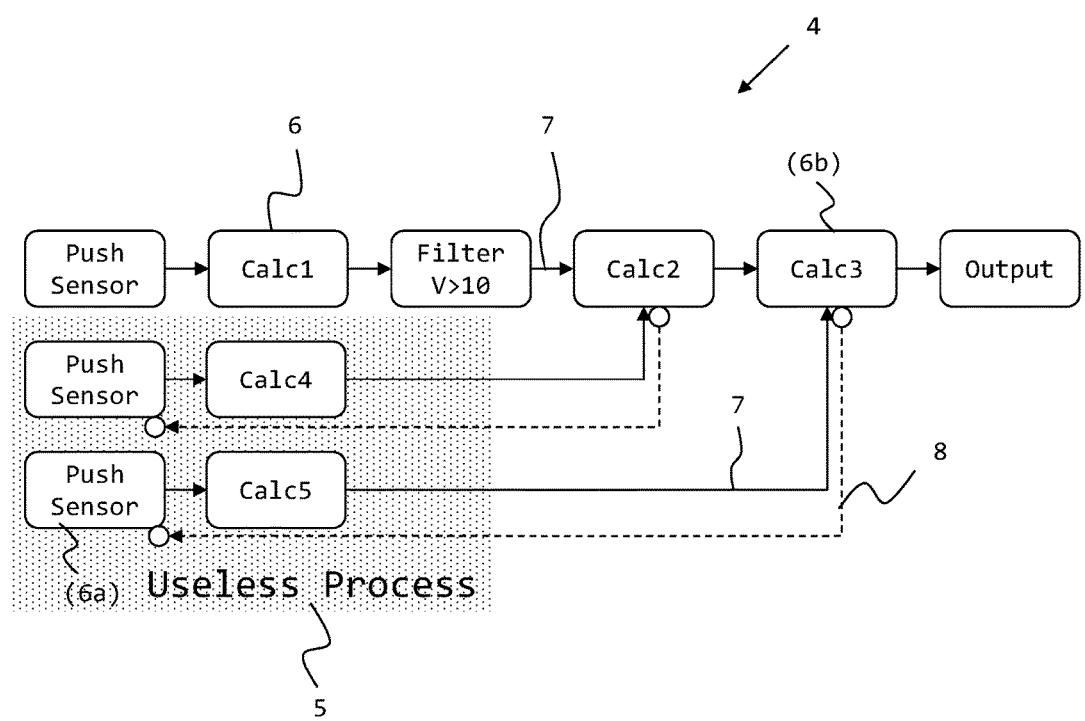
FIG. 2 is a diagram illustrating an example of a process flow built and executed by an event flow system 1.

FIG. 1 is a schematic block diagram of an event flow system according to the present embodiment. FIG. 2 is a diagram illustrating an example of a process flow built and executed by an event flow system 1.

The event flow system 1 connects nodes 6, for which respective processes are defined, from an upstream side to a downstream side by an event 7 which is generated due to a certain process and is used by another process to realize a process flow 4. The event flow system 1 defines respective processes of a plurality of nodes 6 and builds and executes a series of process flows 4 by the plurality of nodes 6 and one or more events 7 that flow between the plurality of nodes 6.

The process flow 4 includes a temporary process 5 which is not regarded to be necessary at all times. The temporary process 5 can be activated when the process is used or can be stopped when the process is not necessary. Activation or stopping of the temporary process 5 is realized using a reverse event 8 that sends a predetermined request from a downstream-side node (a downstream node 6b) to an upstream-side node (an upstream node 6a) contrarily to the event 7.

The relation between the upstream node 6a and the downstream node 6b is relative. If a certain node 6 is a downstream node 6b, a node 6 disposed further toward the upstream side in the flow of the event 7 than the node 6 is an upstream node 6a. Here, the downstream node 6b and the upstream node 6a may not be connected directly by the event 7 and another node 6 may be present between them.

As illustrated in FIG. 1, the event flow system 1 includes a process flow builder 2 and a process flow executer 3. As illustrated in FIG. 2, the process flow builder 2 builds the process flow 4 using a plurality of nodes 6, one or more events 7, and a reverse event 8 that sends a predetermined request from a downstream node 6b to an upstream node 6a. The process flow executer 3 executes the processes defined for the plurality of nodes according to the event 7 and the reverse event 8.

As described above, since a request can be sent from the downstream node 6b to the upstream node 6a by the reverse event 8, it is possible to change an operation of the upstream node 6a on the basis of the state of the downstream node 6b to reduce unnecessary processing. It is possible to build the process flow 4 without using a complex conditional branching logic and to reduce a useless process in execution of the process flow 4.

In this example, the reverse event 8 sends a request for activating or stopping a predetermined process from the downstream node 6b to the upstream node 6a. Since a predetermined process of the upstream node 6a can be activated or stopped from the downstream node 6b, it is possible to activate a process when it is necessary or to stop the process when it is not necessary.

As an example, the reverse event 8 sends a request for activation or stopping of publication of an event by the upstream node 6a. Since publication of an event by the upstream node 6a can be activated or stopped, it is possible to stop an event from the upstream node 6a to the downstream node 6b. Due to this, it is possible to suppress a useless process in the downstream node 6b.

Hereinafter, a more specific embodiment will be described.

(Embodiment)

Figure 3:
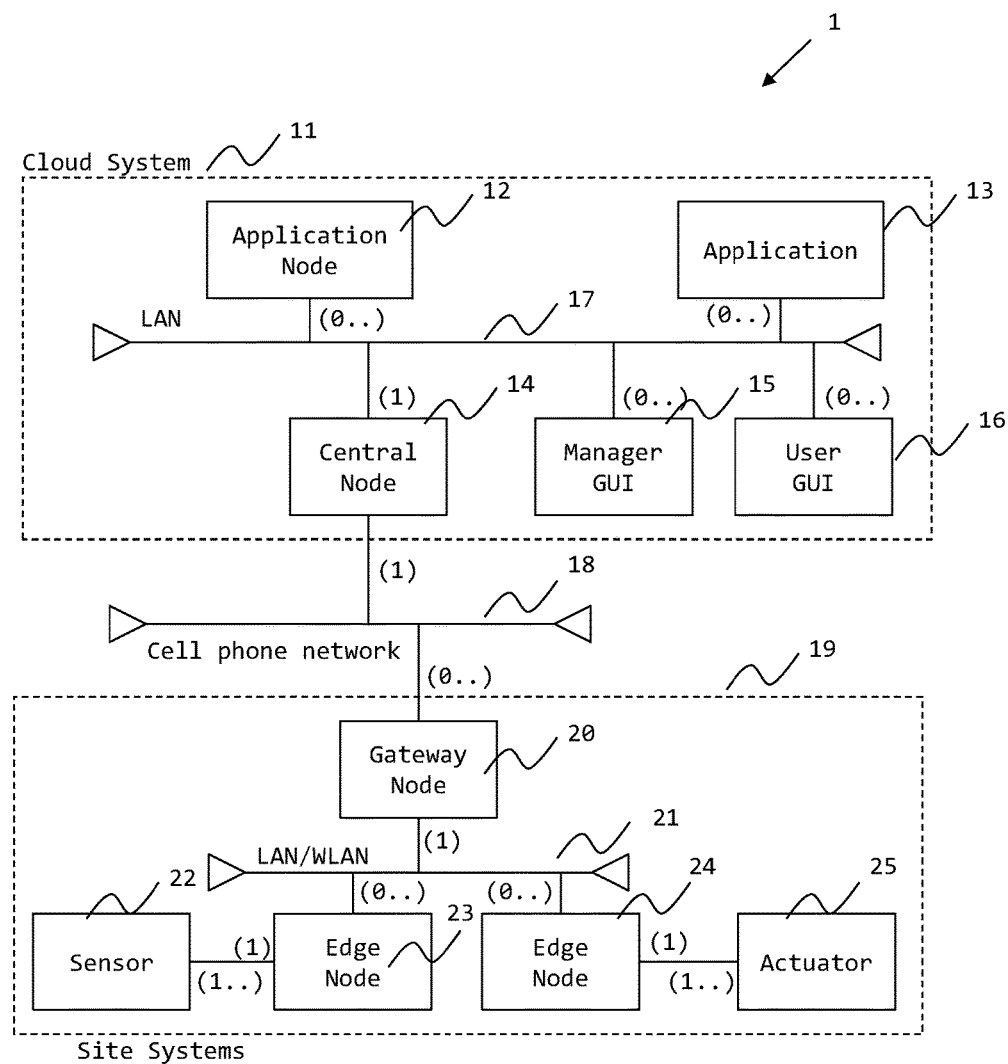
FIG. 3 is a block diagram illustrating an entire configuration of the event flow system according to the present embodiment.

FIG. 3 is a block diagram illustrating an entire configuration of an event flow system according to the present embodiment. The event flow system 1 includes a cloud system 11 and a site system 19. The cloud system 11 and the site system 19 are connected together by a cell phone network 18. In the drawing, the number surrounded by parenthesis indicates an example of the number of target parts to which the number is appended. For example, (1) indicates that the number of target parts is 1 as an example. Moreover, (0. . . ) indicates that the number of target parts is 0 or more as an example.

The event flow system 1 is a monitoring control system as an example and is a system that monitors and controls wind power generation facilities.

The cloud system 11 is disposed in a datacenter of the monitoring control system. The site system 19 is disposed near each of equipment included in the wind power generation facilities.

The site system 19 sends data acquired from respective equipment to the cloud system 11. The cloud system 11 receives the data from respective site systems 19 and stores the data. Moreover, the cloud system 11 analyzes the data to estimate the state of each equipment and determine control to be performed for each equipment. The content of the control on each equipment is notified to the site system 19 as a control instruction. The site system 19 performs control on the equipment according to the notified control instruction.

Many site systems 19 may be connected to one cloud system 11, and the event flow system can function even if the site system 19 is not present.

The cloud system 11 has a configuration in which zero or more application nodes 12, one central node 14, zero or more manager graphic user interfaces (GUIs) 15, and zero or more user GUIs 16 are connected together by a LAN 17.

The application node 12 is a device that executes an application 13. The application 13 is an application program that performs various arithmetic operations using the data collected from respective equipment, for example.

The central node 14 is a main device of the event flow system. The central node 14 builds process flows that respective nodes that include the subject device have to execute. The process flows that respective nodes have to execute are distributed to the nodes that execute the respective process flows and are executed by the nodes. The central node 14 itself also executes a process flow that the central node 14 has to execute.

The manager GUI 15 provides a manager GUI to a manager of the monitoring control system.

The user GUI 16 provides a user GUI to a user of the monitoring control system.

The site system 19 has a configuration in which one or more gateway nodes 20, one or more sensors 22, one edge node 23, one edge node 24, and one or more actuators 25 are connected together by a LAN/WAN 21. The LAN/WAN 21 is a LAN, a WAN, or a communication network in which LAN and WAN are combined.

The gateway node 20 connects to the central node 14 of the cloud system 11 via the cell phone network 18 and sends and receives information including messages and data.

The sensor 22 is various sensors that are disposed in or around equipment to measure the state of or around the equipment.

The edge node 23 connects to the sensor 22 to collect measurement data from the sensor 22 and sends the measurement data to the central node 14 via the gateway node 20.

The edge node 24 receives a control instruction from the central node 14 via the gateway node 20 and controls the actuator 25 according to the control instruction.

The actuator 25 is a movable part that is disposed in or around equipment and is controlled by the edge node 24.

Figure 4:
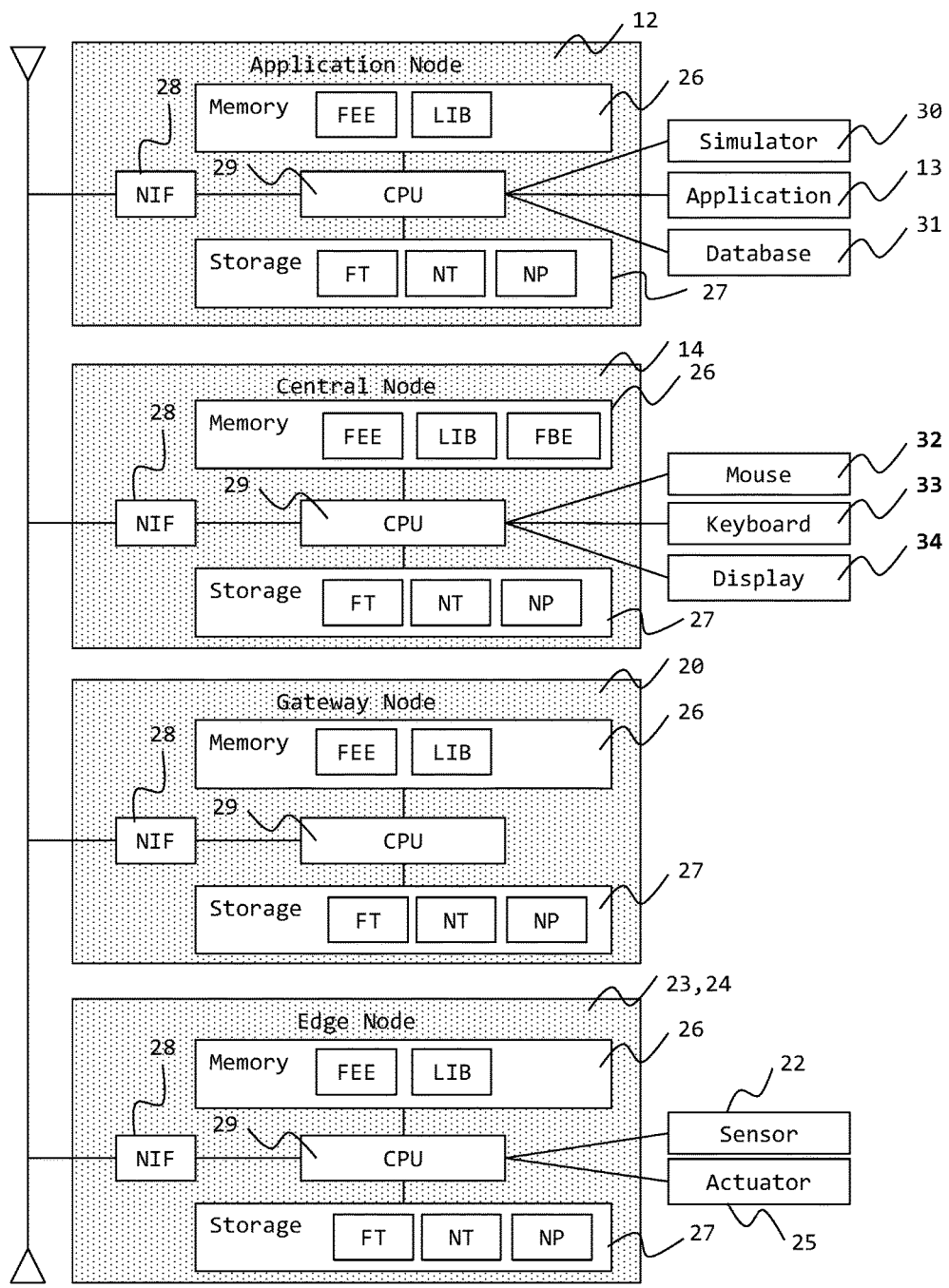
FIG. 4 is a block diagram illustrating a configuration of each node of the event flow system according to the present embodiment.

FIG. 4 is a block diagram illustrating a configuration of each node of the event flow system according to the present embodiment.

The application node 12 includes a memory 26, a storage 27, a network interface (NIF) 28, and a central processing unit (CPU) 29. The memory 26 stores a flow execution engine FEE and a node library LIB. The storage 27 stores a flow table FT, a node table NT, and node parameters NP.

The flow table FT is a table in which information that defines a process flow executed by the application node 12 is stored. The node table NT is a table in which information on nodes included in the process flow is stored. Nodes in the process flow are defined in the node table NT. The node parameters NP are various parameters used in nodes.

The flow execution engine (a process flow executer) FEE is a software program that executes the process flow built by a flow building engine (a process flow builder) FBE of the central node 14. The flow execution engine FEE appropriately uses files in the node library LIB.

The CPU 29 executes a software program such as the flow execution engine FEE on the memory 26. Moreover, the CPU 29 executes a simulator 30 and the application 13 and searches a database 31.

The central node 14 includes a memory 26, a storage 27, a NIF 28, and a CPU 29. The memory 26 stores a flow execution engine FEE, a node library LIB, and a flow building engine FBE. The storage 27 stores a flow table FT, a node table NT, and node parameters NP.

The flow table FT is a table in which information that defines a process flow executed by the central node 14 is stored. The node table NT is a table in which information on nodes included in the process flow is stored. The nodes in the process flow are defined in the node table NT. The node parameters NP are various parameters used in nodes.

The flow building engine FBE is a software program that builds a process flow of the entire monitoring control system. The process flow built by the flow building engine FBE includes process flows that are to be executed by the application node 12, the central node 14, the gateway node 20, and the edge nodes 23 and 24.

The flow execution engine FEE is a software program that executes the process flow built by the flow building engine FBE. The flow execution engine FEE appropriately uses files in the node library LIB.

The CPU 29 executes a software program such as the flow building engine FBE and the flow execution engine FEE on the memory 26. The CPU 29 performs processing using information input from a mouse 32 or a keyboard 33. The CPU 29 displays a processing result and the like on the display 34.

The gateway node 20 includes a memory 26, a storage 27, a NIF 28, and a CPU 29. The memory 12 stores a flow execution engine FEE and a node library LIB. The storage 27 stores a flow table FT, a node table NT, and node parameters NP.

The flow table FT is a table in which information that defines a process flow executed by the gateway node 20 is stored. The node table NT is a table in which information on nodes included in the process flow is stored. The nodes in the process flow are defined in the node table NT. The node parameters NP are various parameters used in nodes.

The flow execution engine FEE is a software program that executes the process flow built by the flow building engine FBE of the central node 14. The flow execution engine FEE appropriately uses files in the node library LIB.

The CPU 29 executes a software program such as the flow execution engine FEE on the memory 26.

The edge node 23 includes a memory 26, a storage 27, a NIF 28, and a CPU 29. The memory 26 stores a flow execution engine FEE and a node library LIB. The storage 27 stores a flow table FT, a node table NT, and node parameters NP.

The flow table FT is a table in which information that defines the process flow executed by the edge node 23 is stored. The process flow of the edge node 23 includes a process of acquiring measurement data from the sensor 22 and notifying the measurement data to the central node 20. The node table NT is a table in which information on nodes included in the process flow is stored. The nodes in the process flow are defined in the node table NT. The node parameters NP are various parameters used in nodes.

The flow execution engine FEE is a software program that executes the process flow built by the flow building engine FBE of the central node 14. The flow execution engine FEE appropriately uses files in the node library LIB.

The CPU 29 executes a software program such as the flow execution engine FEE on the memory 26.

The edge node 24 includes a memory 26, a storage 27, a NIF 28, and a CPU 29. The memory 26 stores a flow execution engine FEE and a node library LIB. The storage 27 stores a flow table FT, a node table NT, and node parameters NP.

The flow table FT is a table in which information that defines the process flow executed by the edge node 24 is stored. The process flow of the edge node 24 includes a process of controlling the actuator 25. The node table NT is a table in which information on nodes included in the process flow is stored. The nodes in the process flow are defined in the node table NT. The node parameters NP are various parameters used in nodes.

The flow execution engine FEE is a software program that executes the process flow built by the flow building engine FBE of the central node 14. The flow execution engine FEE appropriately uses files in the node library LIB.

The CPU 29 executes a software program such as the flow execution engine FEE on the memory 26.

Figure 5:
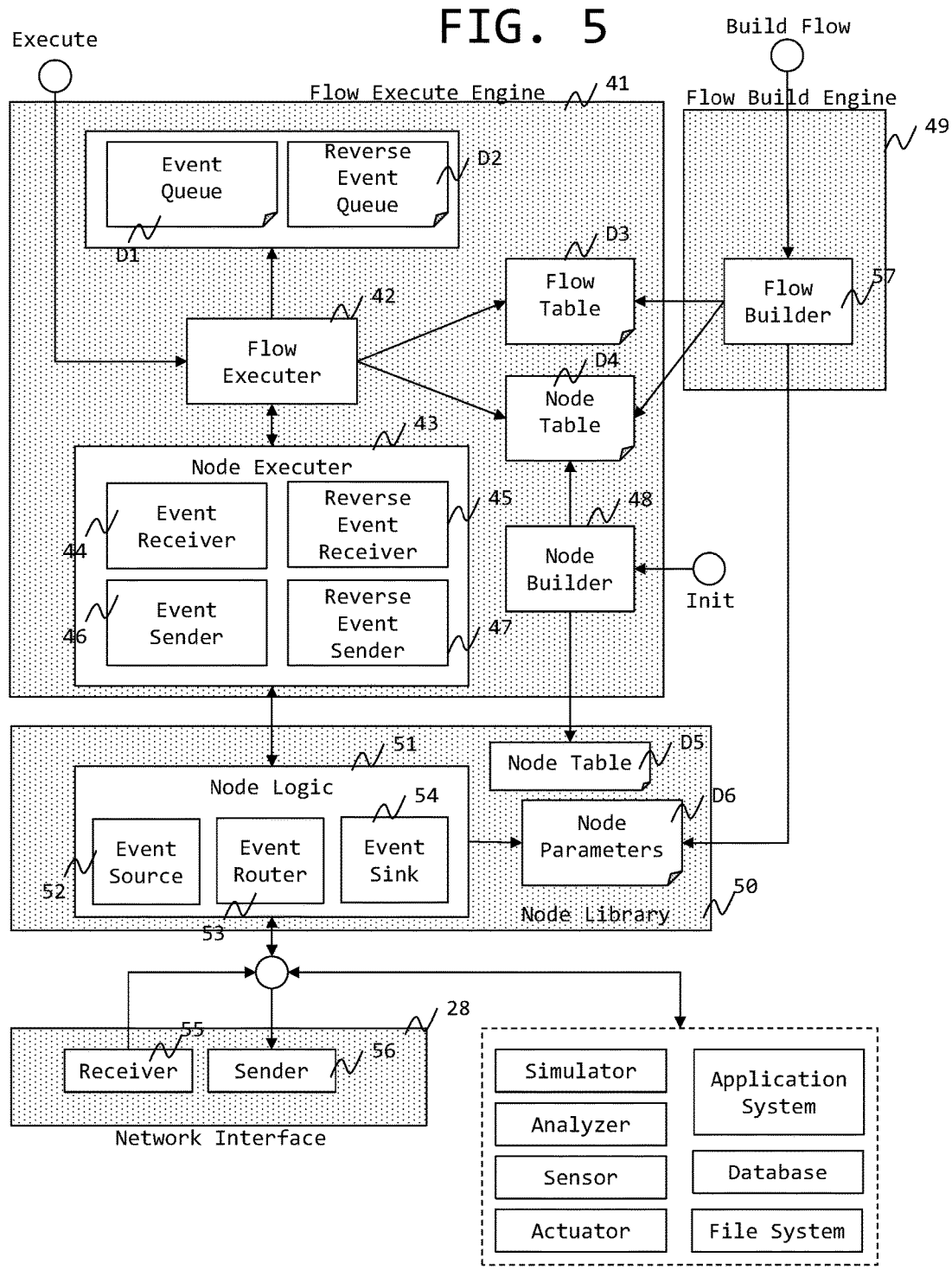
FIG. 5 is a diagram for describing how a central node 14 executes a process.

FIG. 5 is a diagram for describing how the central node 14 executes a process. The central node 14 will be described in detail as a representative node of various nodes since the central node 14 includes the flow building engine that builds a process flow as well as the flow execution engine that executes the process flow. A basic configuration and a basic operation of flow execution engines of other types of nodes are the same as those of the flow execution engine of the central node 14.

The central node 14 includes a flow building engine (FBE) 49, a flow execution engine (FEE) 41, a node library (LIB) 50, and a NIF 28. The central node 14 executes processing in cooperation with a simulator, an analyzer, a sensor, an actuator, an application system, a database, and a file system.

The FBE 49 is a software program that builds a process flow and includes a flow builder 57. The flow builder 57 builds a process flow. Information on the process flow is stored in a flow table D3 and a node table D4.

The FEE 41 is a software program that executes a process flow and includes a flow executer 42, a node executer 43, and a node builder 48. The node executer 43 includes an event receiver 44, a reverse event receiver 45, an event sender 46, and a reverse event sender 47.

The flow executer 42 executes a process flow in cooperation with the node executer 43 with reference to the flow table D3 and the node table D4.

In the node executer 43, the event receiver 44 performs a process for allowing a certain node 6 to receive an event 7 from another node 6. The reverse event receiver 45 performs a process for allowing a certain node 6 to receive a reverse event 8 from another node 6. The event sender 46 performs a process for allowing a certain node 6 to send an event 7 to another node 6. The reverse event sender 47 performs a process for allowing a certain node 6 to send a reverse event 8 to another node 6.

The node builder 48 builds a node 6 in cooperation with the flow builder 57 and stores information on the node 6 in the node table D4 and the node table D5.

The LIB 50 is a library of nodes and includes a node logic 51. The node logic 51 includes an event source 52, an event router 53, and an event sink 54. The event source 52 is a node that generates an event 7 to another node 6. The event router 53 is a node that receives an event 6 from another node 6 and sends an event 7 to still another node 6. The event sink 54 is a node 6 that receives an event 7 from another node 6.

The processing contents of the event source 52, the event router 53, and the event sink 54 are defined on the basis of the node table D5. The event source 52, the event router 53, and the event sink 54 execute processes with reference to node parameters D6.

In the NIF 28, a receiver 55 receives data from a communication network and a sender 56 sends data to the communication network.

Figure 6:
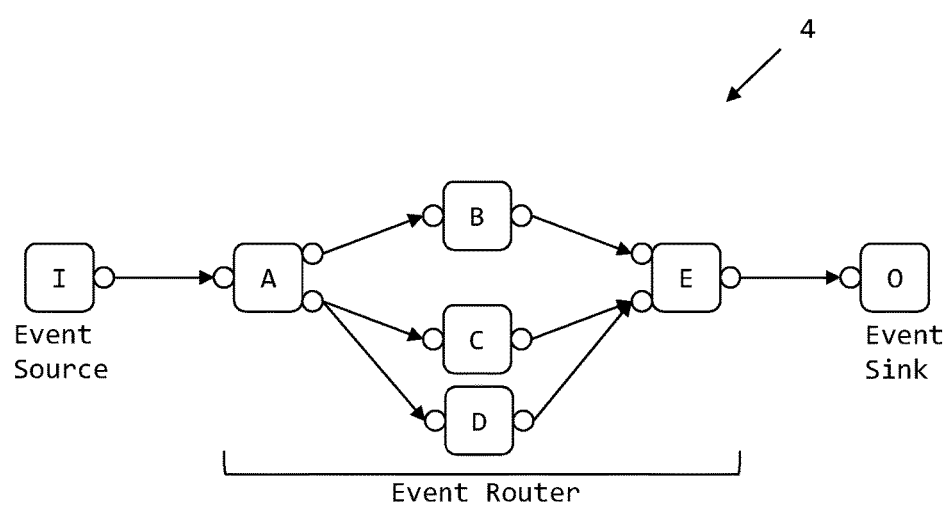
FIG. 6 is a diagram illustrating an example of a process flow.

FIG. 6 is a diagram illustrating an example of a process flow. FIG. 7 is a table illustrating an example of a node table corresponding to the process flow illustrated in FIG. 6. FIG. 8 is a table illustrating an example of a flow table corresponding to the process flow illustrated in FIG. 6.

In FIG. 6, a node I is an event source, nodes A, B, C, and D are event routers, and a node O is an event sink. The flow builder 57 builds such a process flow as illustrated in FIG. 6.

In the process flow in FIG. 6, events from the node I are sent to the node A. One event from the node A is sent to the node B and the other events are sent to the nodes C and D. An event from the node B is sent to the node E. An event from the node C is sent to the node E. An event from the node D is sent to the node E. An event from the node E is sent to the node O.

In FIG. 7, the type (Class) of nodes used in the process flow of FIG. 6 is defined. The node type includes Classes I, A, B, C, D, E, and O. For example, for Class I, an input port number (IN port number) is 0, an output port number (OUT port number) is 1, and a cost (Cost) is 10. The cost in the node table D4 indicates a predetermined time or processing amount required for processing of the node. This cost is a logical value defined by the type of the node.

FIG. 8 describes information on nodes and events used in the process flow of FIG. 6. The type (Class), an input port destination (I0, . . . , In), an output port destination (O0, O1, . . . , On), and a cost (Cost) of each node are described. For example, for the node I, the type is Class I, the output port O0 is connected to A#I0, and the cost is 11. A#I0 indicates an input port I0 of the node A. The cost of the flow table D3 indicates a time or a processing amount required for processing when processing is actually executed. This cost is a measured value when processing is actually executed.

Figure 9:
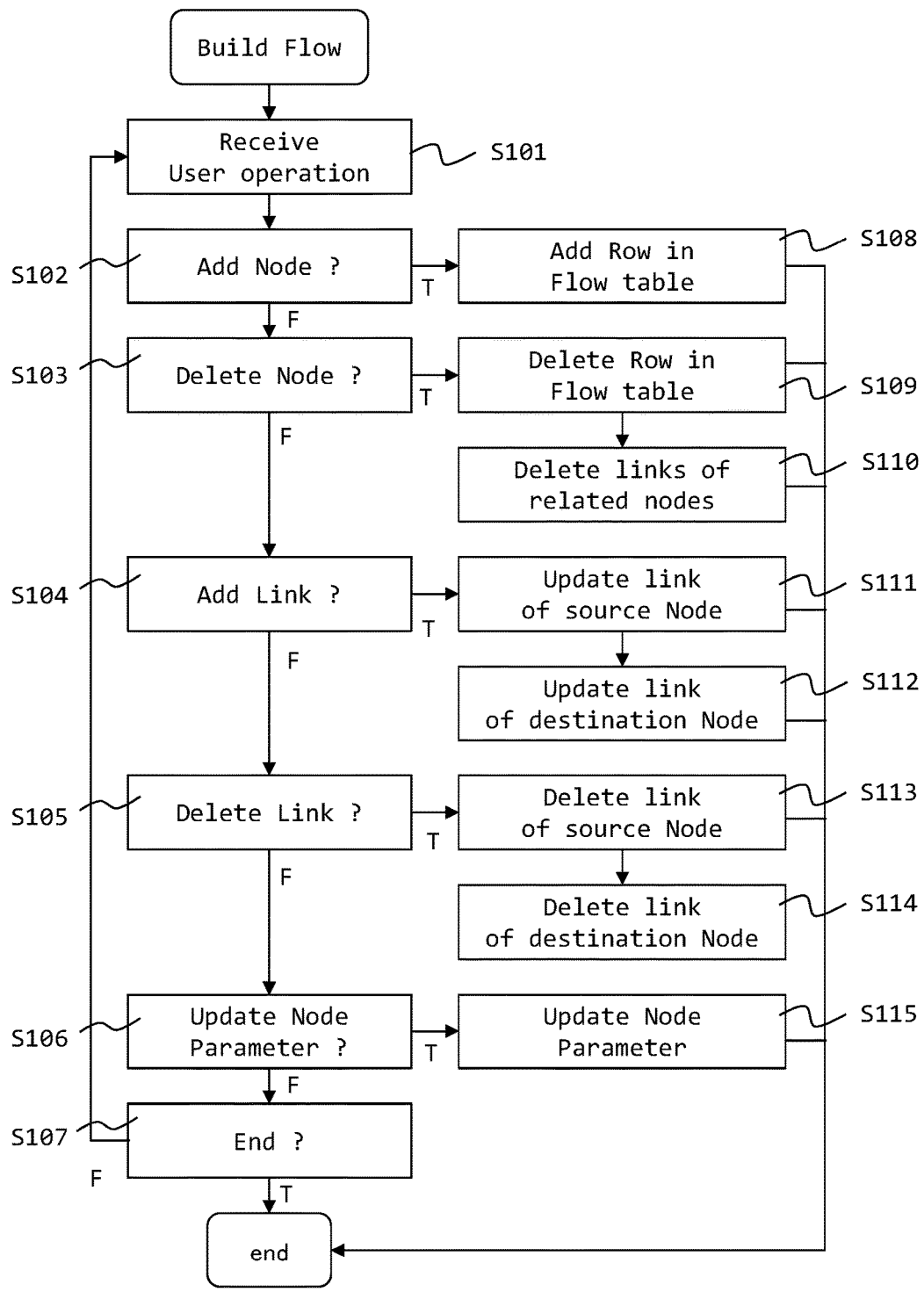
FIG. 9 is a flowchart illustrating a process executed by a flow builder.

FIG. 9 is a flowchart illustrating a process executed by the flow builder.

Upon receiving a user operation in step S101, the flow builder 57 determines whether the user operation is a node addition request in step S102. When the user operation is not anode addition request, the flow builder 57 determines whether the user operation is a node deletion request in step S103.

When the user operation is not a node deletion request, the flow builder 57 determines whether the user operation is a link addition request in step S104. A link is a connection between nodes indicating an event or a reverse event. When the user operation is not a link addition request, the flow builder 57 determines whether the user operation is a link deletion request in step S105.

When the user operation is not a link deletion request, the flow builder 57 determines whether the user operation is a node parameter update request in step S106. When the user operation is not a node parameter update request, the flow builder 57 determines whether the user operation is an end request in step S107. When the user operation is not an end request, the flow builder 57 returns to step S101. When the user operation is an end request, the flow builder 57 ends the process.

When it is determined in step S102 that the user operation is a node addition request, the flow builder 57 adds a row of a node corresponding to the addition request to the flow table D3 in step S108. When it is determined in step S103 that the user operation is a node deletion request, the flow builder 57 deletes a row of a node corresponding to the deletion request from the flow table D3 in step S109. Furthermore, the flow builder 57 searches for another row of the flow table to delete links of related nodes in step S110.

When it is determined in step S104 that the user operation is a link addition request, the flow builder 57 adds link information (destination information) to a source node of a link corresponding to the addition request to the flow table D3 in step S111. Furthermore, the flow builder 57 adds link information (source information) to a destination node of a link corresponding to the addition request in step S112.

When it is determined in step S105 that the user operation is a link deletion request, the flow builder 57 deletes source information of a link corresponding to the deletion request from the flow table D3 in step S113. Furthermore, the flow builder 57 deletes destination information of a link corresponding to the deletion request from the flow table D3 in step S114.

When it is determined in step S106 that the user operation is a node parameter update request, the flow builder 57 update the requested node parameters of the flow table D3 in step S115.

Figure 10:
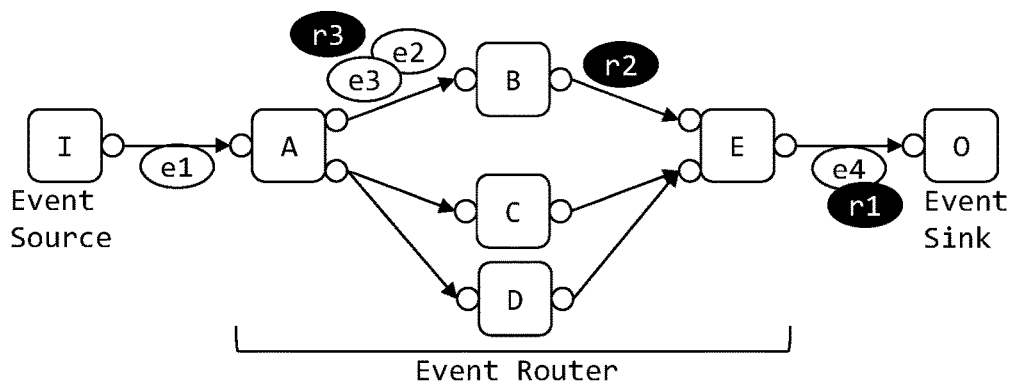
FIG. 10 is a diagram for describing how a flow executer executes a process flow.

FIG. 10 is a diagram for describing how a flow executer executes a process flow. FIG. 11 is a table illustrating an example of an event queue corresponding to an execution state of the process flow illustrated in FIG. 10. FIG. 12 is a table illustrating an example of a reverse event queue corresponding to an execution state of the process flow illustrated in FIG. 10.

The event queue D1 includes a source (FROM) and a destination (TO) of an event, an event name (EVENT), and a remaining time (Limit) to a processing time limit. A value in the field of Limit is counted down with the elapse of time. For example, if the unit of Limit is [minute], since the Limit of an event e1 is 10, it is necessary to process the event e1 within 10 minutes. The items described in the reverse event queue D2 are the same as those of the event queue D1.

As illustrated in FIG. 5, the flow executer 42 stores the received events in the event queue D1, stores the received reverse events in the reverse event queue D2 if necessary, calls an event from the event queue D1, and calls a reverse event from the reverse event queue D2 if necessary to execute a predetermined process. The flow executer 42 sends a processing result as an event or a reverse event or both if necessary.

In FIG. 10, an outlined ellipse indicates an event stored in the event queue D1 and an event name is written in the outlined ellipse. Moreover, a dark ellipse indicates a reverse event stored in the reverse event queue D2 and a reverse event name is written in the dark ellipse.

Referring to FIG. 10, for example, an outlined ellipse of the event e1 is illustrated near a link indicating an event from the node I to the node A. Referring to FIG. 11, the source of the first event e1 is an output port O0 of the node I and the destination thereof is an input port I0 of the node A. Moreover, the event e1 needs to be processed within 10 minutes as described above.

Referring to FIG. 10, for example, a dark ellipse of the reverse event r1 is illustrated near a link indicating an event from the node E to the node O. Referring to FIG. 12, the source of the first reverse event r1 is an input port I0 of the node O and the destination thereof is an output port O0 of the node E. Moreover, the reverse event r1 needs to be processed within 10 minutes.

FIG. 13 is a sequence diagram illustrating an example of how an event flows between nodes due to execution of a process flow. In the example of FIG. 13, the event e1 is sent from the node A to the node C, and the event e2 is sent from the node B to the node C. The node C receives the events e1 and e2 and sends the event e3 to the node D.

FIG. 14 is a sequence diagram illustrating another example of how an event flows between nodes due to execution of a process flow. In the example of FIG. 14, the event e4 is sent from the node E to the node G and the event e6 is sent from the node F to the node G. The node G sends the event e5 to the node H upon receiving the event e4 from the node E and sends the event e7 to the node H upon receiving the event e6.

Figure 15:
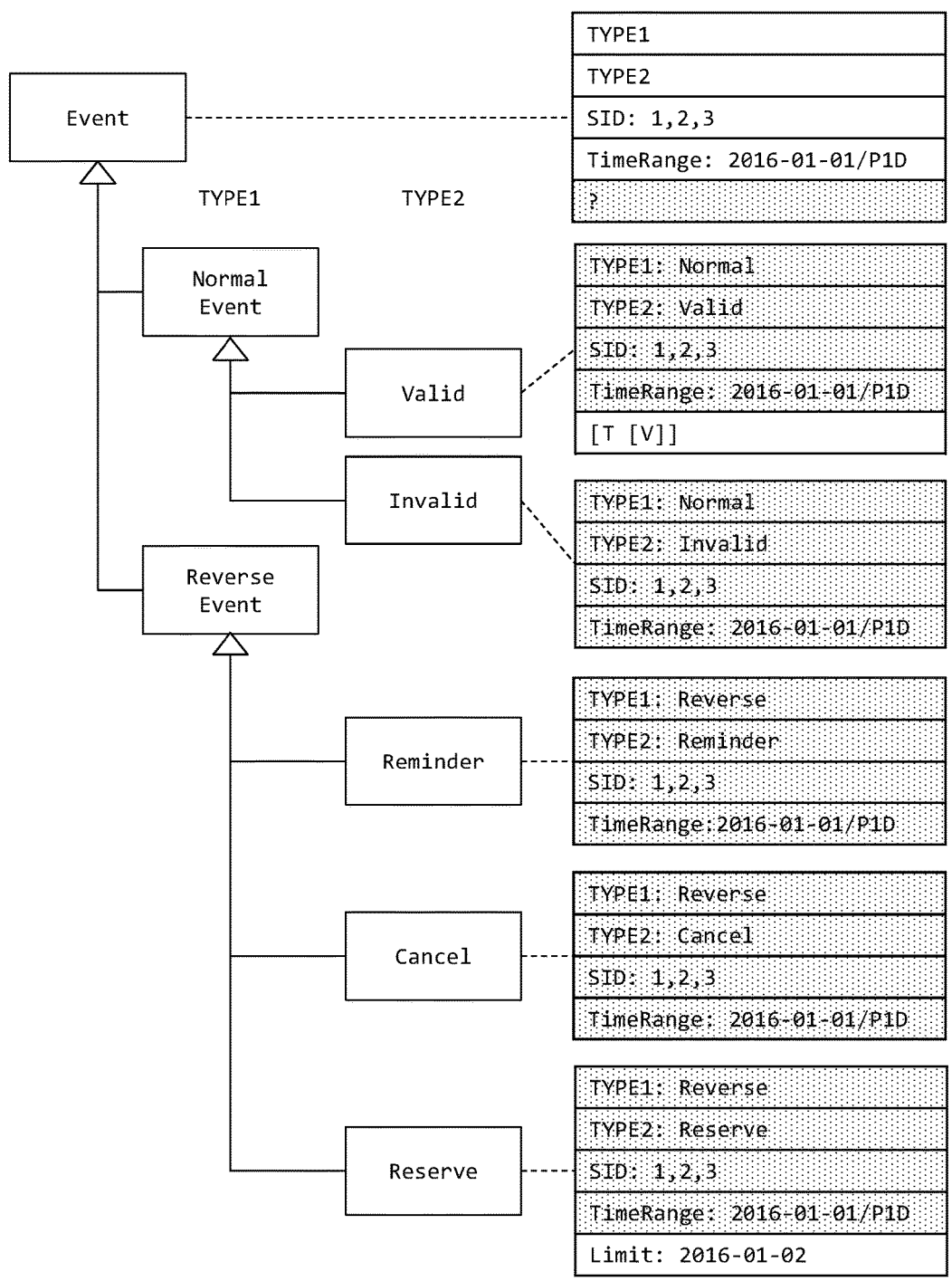
FIG. 15 is a diagram illustrating the types and the contents of an event and a reverse event.

FIG. 15 is a diagram illustrating the types and the contents of an event and a reverse event. Event information includes Type 1 (TYPE1), Type 2 (TYPE2), a sensor ID (SID), and a time range (TimeRange) as the content thereof. Type 1 indicates a broader type and Type 2 indicates a detailed type. The sensor ID is identification information of a sensor that measures measurement data related to an event. The time range indicates a time range such as one day in the case of information on a certain time range.

The event includes an event (a normal event) and a reverse event. Whether the event is a normal event or a reverse event is indicated by Type 1.

The normal event includes a valid (Valid) event and an invalid (Invalid) event. Whether the event is valid or invalid is indicated by Type 2. A valid event may include data T [V].

The reverse event includes Reminder, Cancel, and Reserve. Whether the reverse event is Reminder, Cancel, or Reserve is indicated by Type 2.

The reminder is a message that requests activation of publication of an event. By using the reminder message, it is possible to stop publication of an event in a normal time and to activate publication of an event when it is necessary. Therefore, it is possible to suppress publication of a useless event.

Cancel is a message that request deletion of events generated by an upstream node and stored in a queue. By using the Cancel message, since it is possible to cancel stored data, it is possible to delete data which results in publication of a useless asynchronous event and to reduce a processing load of asynchronous events.

The reserve is a message that sets a deadline time of publication of an event by an upstream node. The reserve includes an event publication deadline time (Limit). By using the reserve message and setting a deadline time for publication of an event to an event having a low urgency level, it is possible to allow an upstream node to perform a process having a high urgency level preferentially and to distribute a processing load in time.

Figure 16:
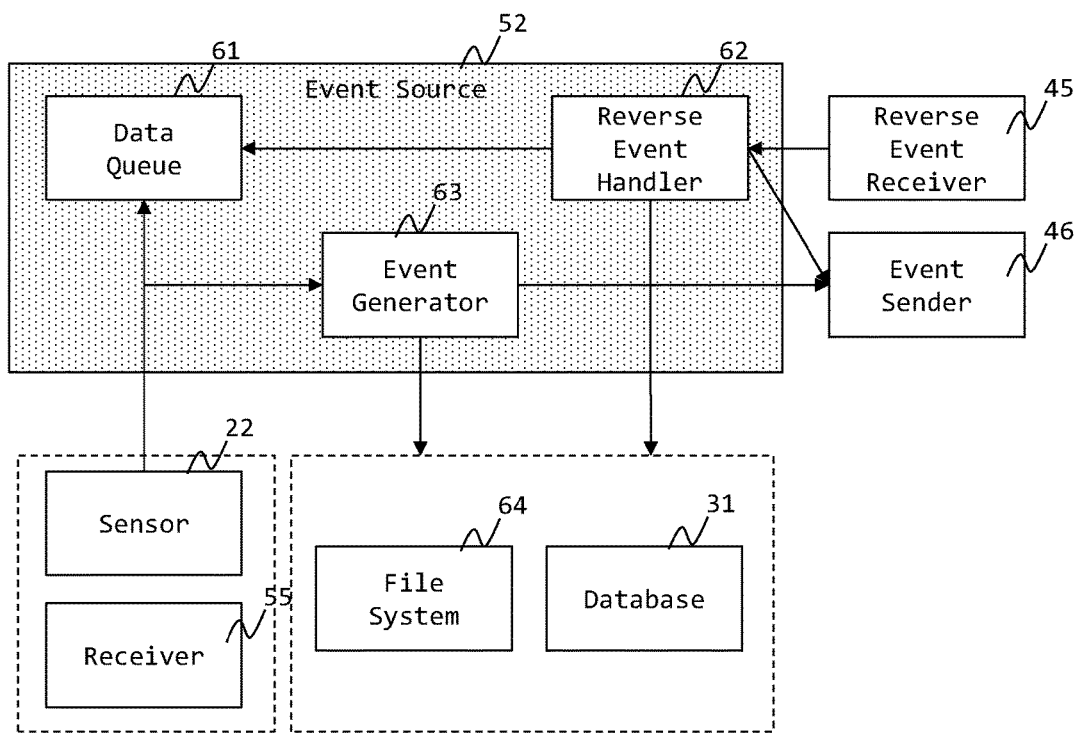
FIG. 16 is a block diagram illustrating a configuration of an event source.

FIG. 16 is a block diagram illustrating a configuration of an event source. The event source 52 includes a data queue 61, a reverse event handler 62, and an event generator 63.

The data input from the sensor 22 or the receiver 55 is primarily stored in the data queue 61. The event generator 63 extracts data from the data queue 61 at a predetermined timing, processes the data to generate an event, and sends the event to the event sender 46. In the case of the event source 52 that processes data immediately, the event generator 63 starts processing immediately when data is stored in the data queue 61. In the case of the event source 52 that stores and processes data, the event generator 63 extracts data from the data queue 61 at a fixed time interval, for example, and processes the data. The reverse event handler 62 operates according to the request of a reverse event upon receiving the reverse event from the reverse event receiver 45. The event generator 63 and the reverse event handler 62 refer to data of a file system 64 and a database 31 appropriately and uses the data for processing.

When the reverse event is Reminder, the reverse event handler 62 enables the data queue 61 to be readable and activates publication of a stopped event. When the reverse event is Cancel, the reverse event handler 62 deletes the data stored in the data queue 61. When the reverse event is Reserve, the reverse event handler 62 sets a time limit (a deadline time) for sending an event based on the data stored in the data queue 61.

Figure 17:
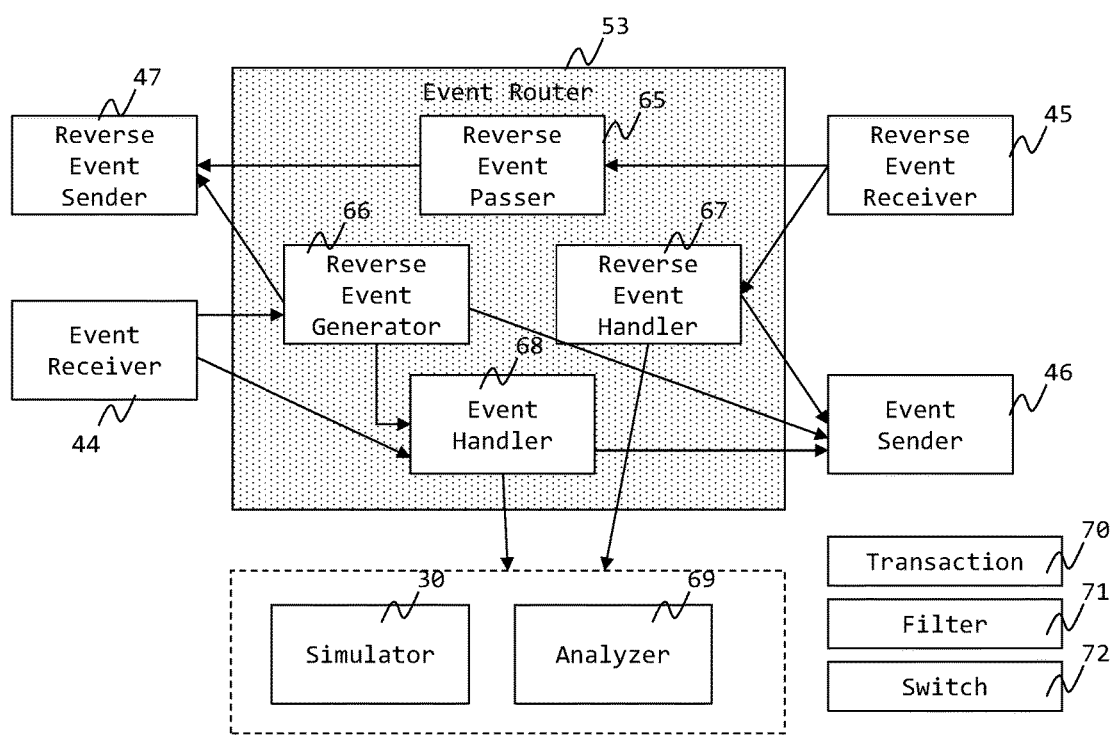
FIG. 17 is a block diagram illustrating a configuration of an event router 53.

FIG. 17 is a block diagram illustrating a configuration of the event router 53. The event router 53 includes a reverse event passer 65, a reverse event generator 66, a reverse event handler 67, and an event handler 68.

The event handler 68 processes an event input from the event receiver 44, generates an event, and sends the event to the event sender 46. The reverse event generator 66 generates a reverse event on the basis of the event input from the event receiver 44 and sends the reverse event to the reverse event sender 47.

When the reverse event input from the reverse event receiver 45 is an event that is to be processed by the event router 53, the reverse event is sent to the reverse event handler 67. The reverse event handler 67 processes the received reverse event and operates according to the request of the reverse event.

When the reverse event is Reminder, the reverse event handler 67 activates publication of a stopped event. When the reverse event is Cancel, the reverse event handler 67 deletes the data stored in a data queue (not illustrated). When the reverse event is Reserve, the reverse event handler 67 sets a time limit (a deadline time) for sending an event based on the data stored in a data queue (not illustrated).

When the reverse event input from the reverse event receiver 45 is not an event that is to be processed by the event router 53, the reverse event is sent to the reverse event sender 47 by the reverse event passer 65.

The event handler 68 and the reverse event handler 67 appropriately use the simulator 30 that executes simulation or an analyzer 69 that analyzes data. Moreover, the event router 53 appropriately cooperates with a transaction 70, a filter 71, or a switch 72.

Figure 18:
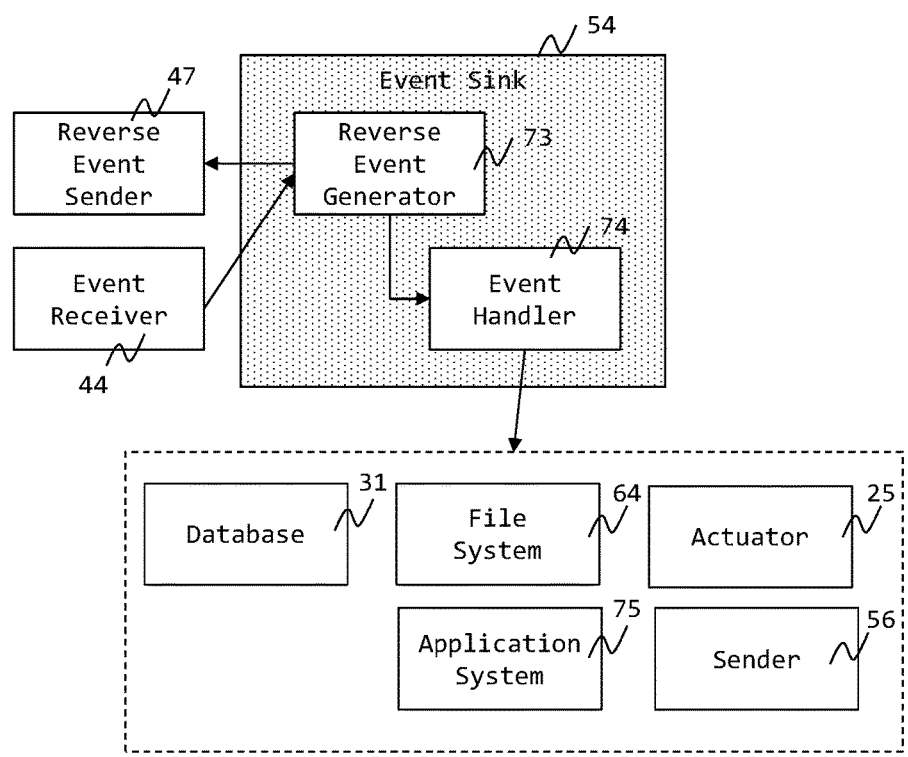
FIG. 18 is a block diagram illustrating a configuration of an event sink.

FIG. 18 is a block diagram illustrating a configuration of an event sink. The event sink 54 includes a reverse event generator 73 and an event handler 74.

The event input from the event receiver 44 is received by the reverse event generator 73. The reverse event generator 73 processes the received event, generates a reverse event as necessary, and sends the reverse event to the reverse event sender 47. Moreover, the reverse event generator 73 sends the received event to the event handler 74. The event handler 74 performs a predetermined process on the event. The event handler 74 cooperates with a database 31, a file system 64, an actuator 25, an application system 75, and a sender 56 appropriately. For example, the event handler 74 acquires predetermined data from the database 31 and the file system 64 according to an application program of the application system 75, processes an event using the data, controls the actuator 25, and sends data via the sender 56.

Figure 19:
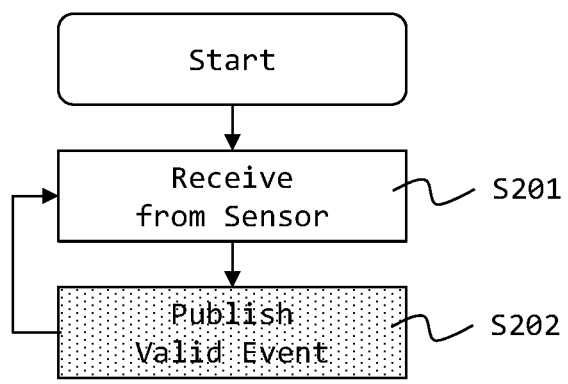
FIG. 19 is a flowchart illustrating a process executed by an event generator.
Figure 20:
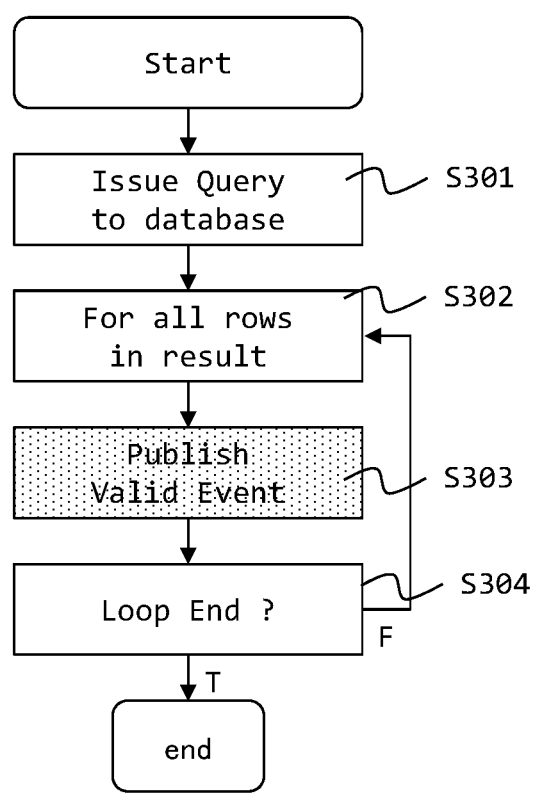
FIG. 20 is a flowchart illustrating a process executed by an event generator.
Figure 21:
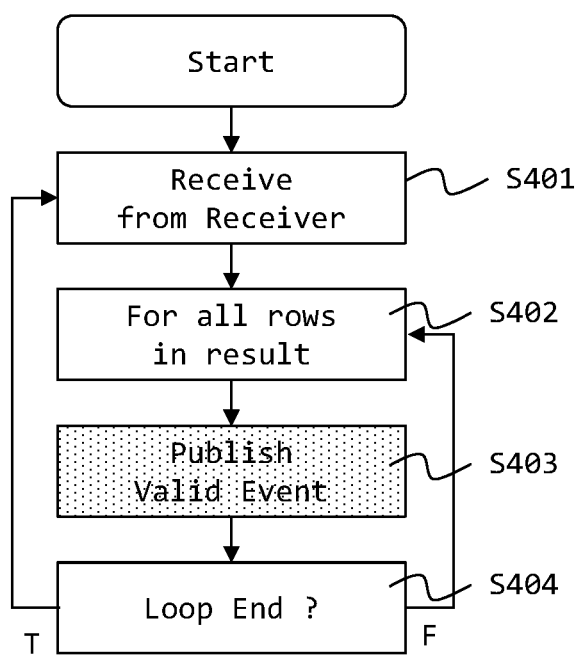
FIG. 21 is a flowchart illustrating a process executed by an event generator.

FIGS. 19, 20, and 21 are flowcharts illustrating a process executed by the event generator.

FIG. 19 illustrates a process of the event generator 63 when measurement data is received from the sensor 22. Referring to FIG. 19, upon receiving measurement data from the sensor 22 in step S201, the event generator 63 publishes a valid event (step S202).

FIG. 20 illustrates a process of the event generator 63 when an event of the data acquired from the database 31 is published. Referring to FIG. 20, first, the event generator 63 issues a desired query to the database 31 and extracts data to be notified by an event. Subsequently, the event generator 63 publishes a valid event (step S303) for all rows of the extracted data (step S302). When publication of an event ends for all items of extracted data (step S304), the event generator 63 ends the process.

FIG. 21 illustrates a process of the event generator 63 when the event of the data received from the receiver 55 is published. Referring to FIG. 21, the event generator 63 receives data from the receiver 55 in step S401. Subsequently, the event generator 63 publishes a valid event (step S403) for all rows of received data (step S402). When publication of an event ends for all items of received data (step S404), the event generator 63 waits for reception of the next data.

Figure 22:
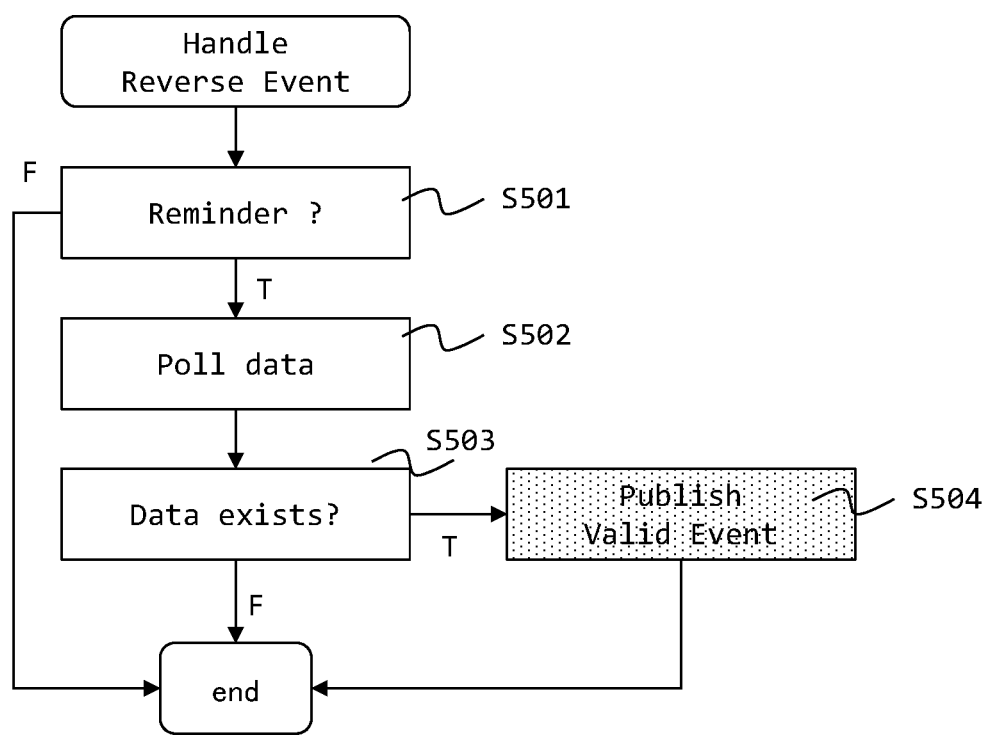
FIG. 22 is a flowchart illustrating a process executed by a reverse event handler of an event source.

FIG. 22 is a flowchart illustrating a process executed by a reverse event handler of an event source. The reverse event handler 62 of the event source 52 determines whether Type 2 of a target reverse event is Reminder in step S501. When the reverse event is not Reminder, the reverse event handler 62 ends the process. When the reverse event is Reminder, the reverse event handler 62 polls data to be sent by an event in step S502 and determines the presence of data to be sent in step S503. When data is present, the reverse event handler 62 publishes a valid data based on the data in step S504. When data is not present, the reverse event handler 62 ends the process.

Figure 23:
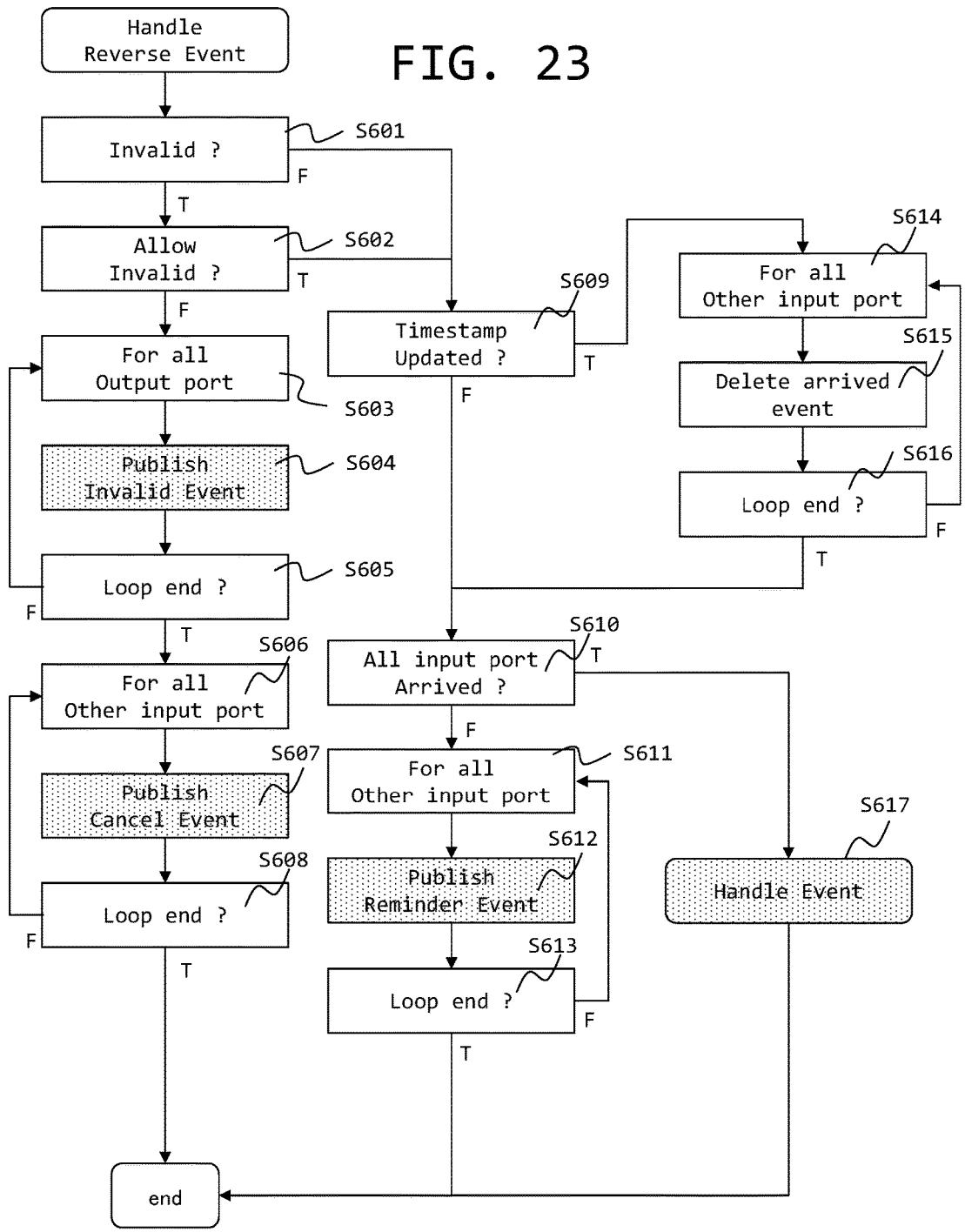
FIG. 23 is a flowchart illustrating a process executed by a reverse event generator.

FIG. 23 is a flowchart illustrating a process executed by a reverse event generator. The event router 53 includes the reverse event generator 66, and the event sink 54 includes a reverse event generator 73. The process illustrated in FIG. 23 is a process common to these elements. In this example, the reverse event generator 66 will be described as an example.

First, the reverse event generator 66 determines whether an input event is invalid in step S601. When the event is invalid, the reverse event generator 66 determines whether an invalid event is allowed. When an invalid event is not allowed, the reverse event generator 66 publishes an invalid event for all output ports (steps S603 to S605). Furthermore, the reverse event generator 66 publishes a reverse event of Cancel to all input ports (steps S606 to S608) and ends the process.

When it is determined in step S601 that the event is valid or it is determined in step S602 that an invalid event is allowed, the reverse event generator 66 determines whether a timestamp is updated in step S609. When the timestamp is updated, the reverse event generator 66 deletes events arrived for all other input ports (steps S614 to S616).

When it is determined in step S609 that the timestamp is not updated or when it is determined in step S616 that all events have been deleted, the reverse event generator 66 determines whether events have arrived at all input ports in step S610. When events have arrived at all input ports, the reverse event generator 66 asks the event handler 68 to process these events in step S617 and ends the process.

On the other hand, when it is determined in step S610 that events have not arrived at all input ports, the reverse event generator 66 publishes a reverse event of Reminder for all remaining input ports (steps S611 to S613) and ends the process.

Figure 24:
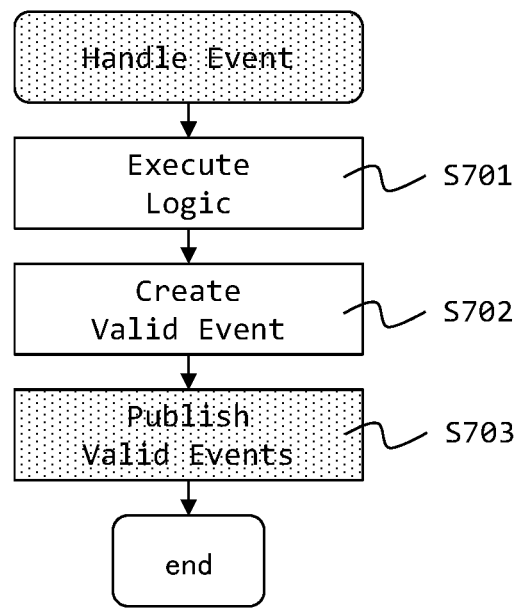
FIG. 24 is a flowchart illustrating a process executed by an event handler.
Figure 25:
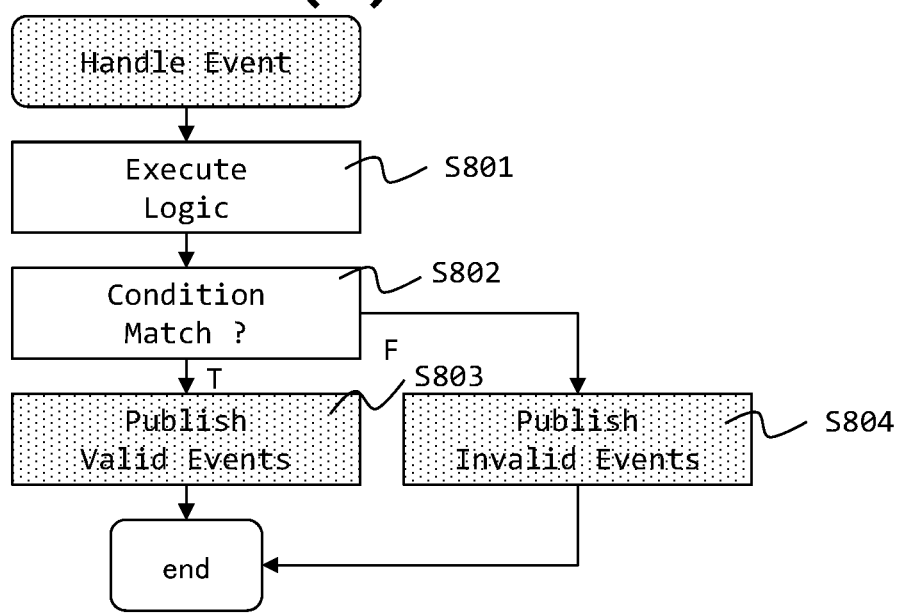
FIG. 25 is a flowchart illustrating a process executed by an event handler.
Figure 26:
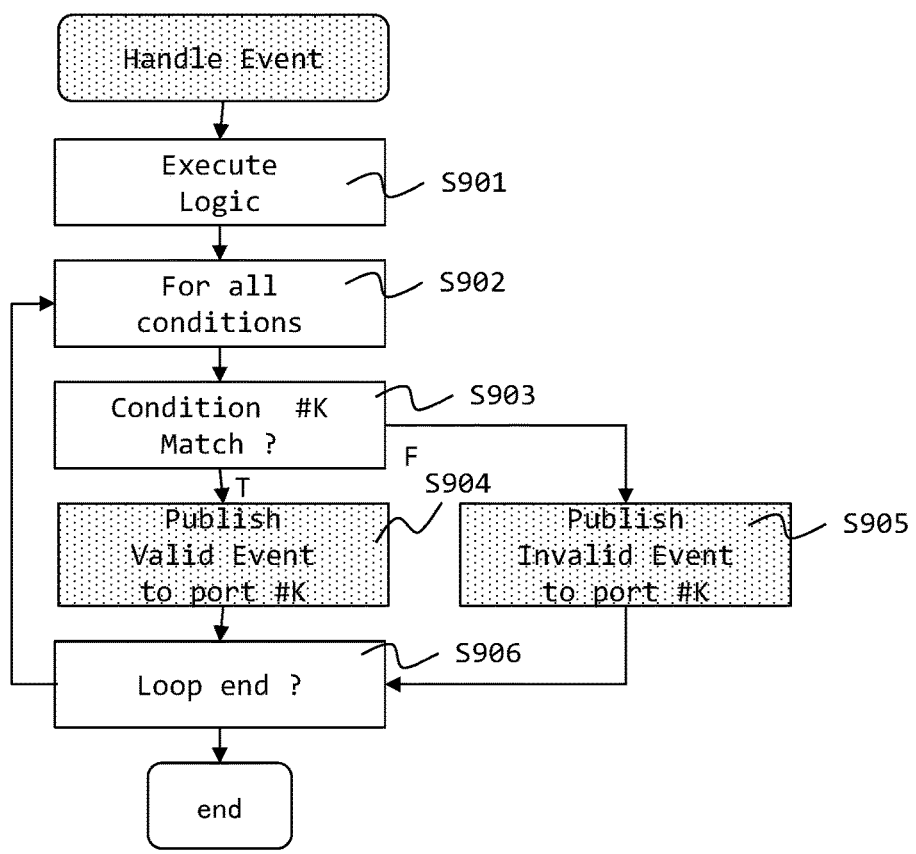
FIG. 26 is a flowchart illustrating a process executed by an event handler.

FIGS. 24, 25, and 26 are flowcharts illustrating a process executed by an event handler. An event handler includes the event handler 68 of the event router 53 illustrated in FIG. 17 and the event handler 74 of the event sink 54 illustrated in FIG. 18. The operations of these elements are basically the same. In this example, the event handler 68 will be described as an example.

FIG. 24 illustrates an operation of an event handler during a transaction process. First, the event handler 68 executes a predetermined logical operation process (step S701) and generates a valid event (step S702). Subsequently, the event handler 68 publishes a valid event (step S703).

FIG. 25 illustrates an operation of an event handler including a filter process. First, the event handler 68 executes a predetermined logical operation process (step S801) and determines whether a predetermined condition is satisfied after the process is executed (step S802). Subsequently, the event handler 68 publishes a valid event if the condition is satisfied (step S803) and publishes an invalid event if the condition is not satisfied (step S804).

FIG. 26 illustrates an operation of an event handler including a switch process. First, the event handler 68 executes a predetermined logical operation process (step S901). Subsequently, the event handler 68 repeats the following loop process for a plurality of conditions (steps S902 to S906).

In the loop process, first, the event handler 68 determines whether the condition is satisfied (step S903), publishes a valid event if the condition is satisfied (step S904), and publishes an invalid event if the condition is not satisfied (step S905).

Figure 27:
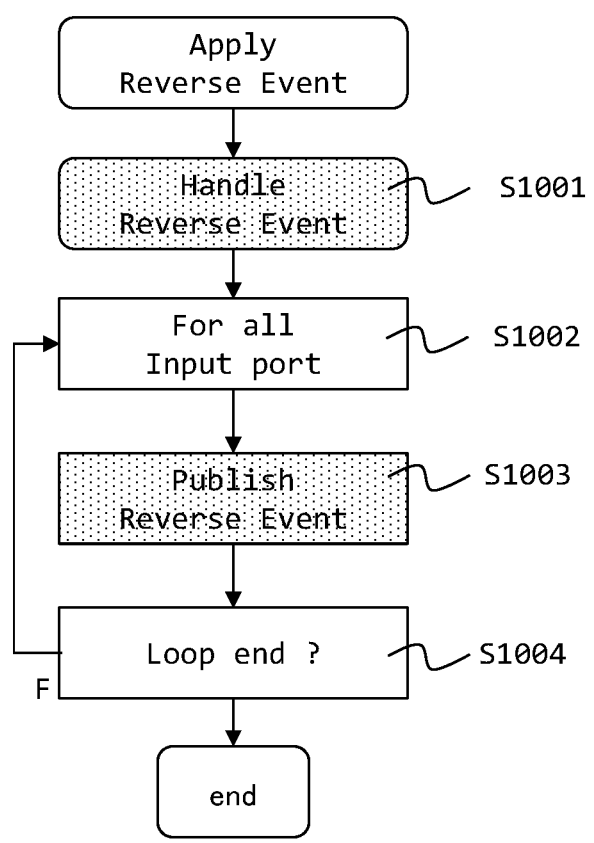
FIG. 27 is a flowchart illustrating a process executed by a reverse event passer of an event router.

FIG. 27 is a flowchart illustrating a process executed by a reverse event passer of an event router. When a reverse event is applied to the event router 53, the reverse event passer 65 executes the following loop process for all input ports after the reverse event is processed by the reverse event handler 67 or when the reverse event is not a processing target of the event router 53 (steps S1002 to S1004). In the loop process, the reverse event passer 65 publishes a reverse event from an input port (step S1003). In this way, the reverse event is sent to an upstream-side node as necessary.

Figure 28:
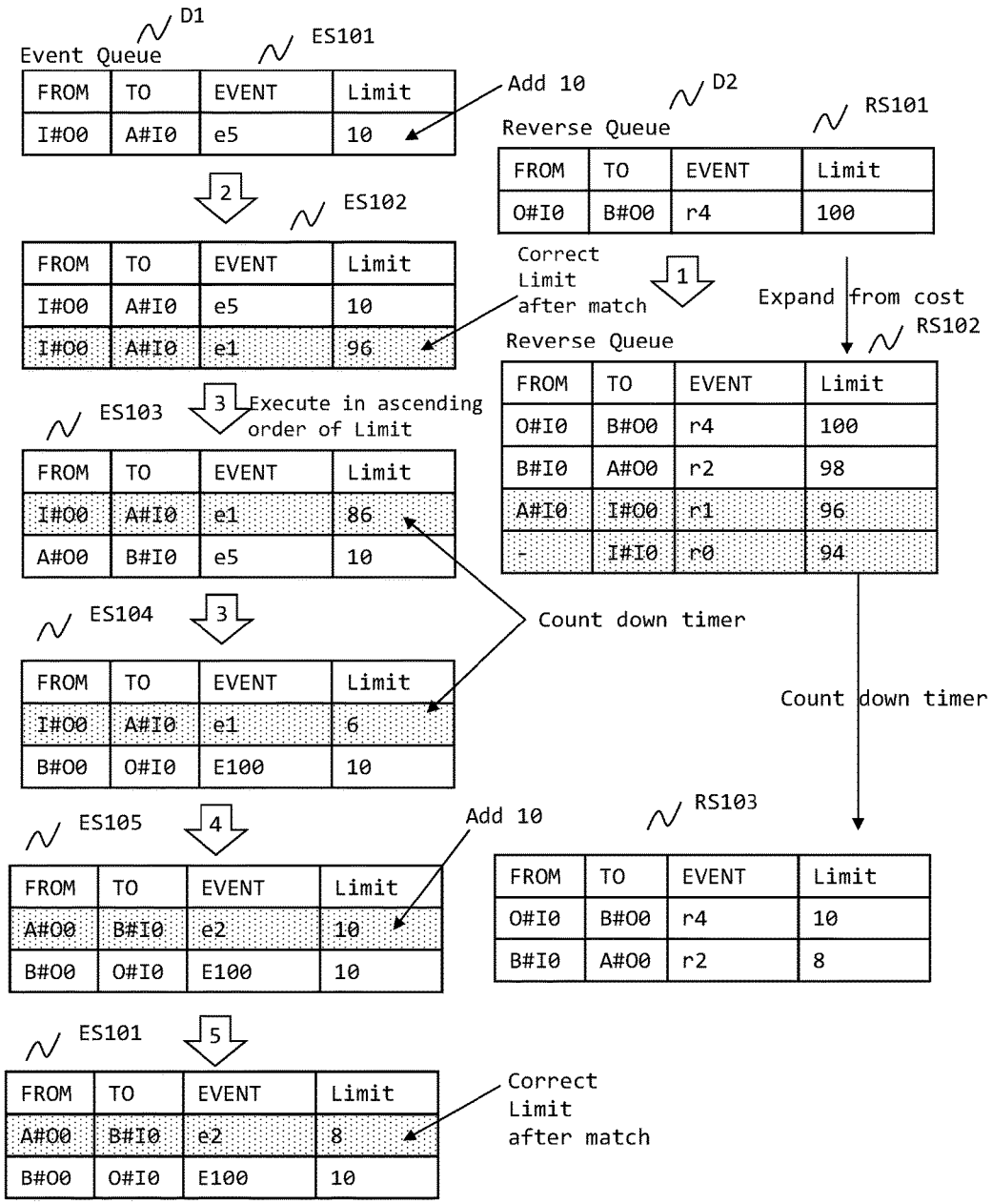
FIG. 28 is a diagram for describing an image of a process of a reverse event of reserve in a process flow.
Figure 29:
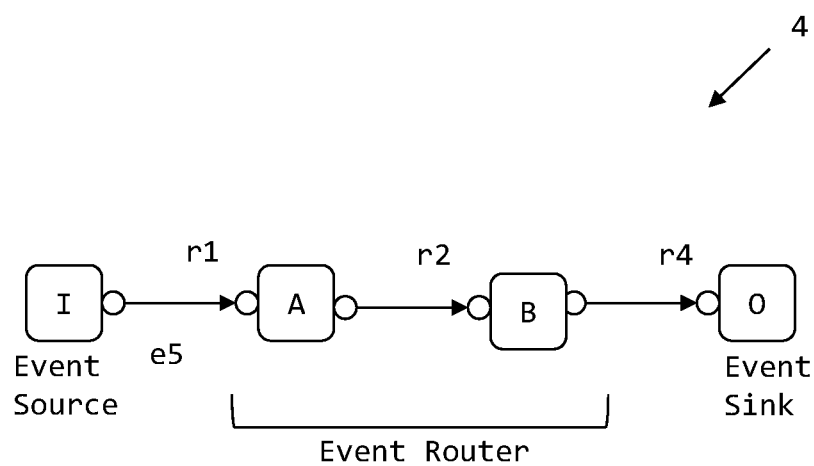
FIG. 29 is a diagram illustrating a certain state of the process flow illustrated in FIG. 28.

FIG. 28 is a diagram for describing an image of a process of a reverse event of Reserve in a process flow. FIG. 29 is a diagram illustrating a certain state of the process flow illustrated in FIG. 28. Referring to FIG. 29, the process flow 4 is configured such that an event is sent from the node I to the node A, an event is sent from the node A to the node B, and an event is sent from the node B to the node O. An event e5 directed from the node I to the node A is illustrated. Moreover, a reverse event r1 directed from the node A to the node I, a reverse event r2 directed from the node B to the node A, and a reverse event r4 directed from the node O to the node B are illustrated.

FIG. 28 illustrates a transition of an event queue D1 on the left side and illustrates a transition of a reverse event queue D2 on the right side.

In state RS101, a reverse event r4 of Reserve directed from the node O to the node B is present in the reverse event queue D2. The reverse event r4 indicates that a remaining time (Limit) to the processing time limit in the node B is 100. The reverse event r4 of Reserve is expanded on the upstream side. In state RS102 in which the reverse event r4 is expanded, the reverse event r4 is expanded to a reverse event r2 indicating that the Limit of the node A is 96, a reverse event r1 indicating that the Limit of the node I is 96, and a reverse event r0 indicating that an input Limit to the node A is 94. The values of the respective Limits are calculated by subtracting the cost of each node whenever tracing nodes upstream. In the example of FIG. 28, the costs of the nodes B, A, and I are calculated as 2.

On the other hand, in state ES101, an event e5 directed from the node I to the node A is present in the event queue D1. In the next state ES102, an event e1 directed from the node I to the node A is added to the event queue D1. In this example, it is assumed that the event e1 has the same SID as the reverse event r1. Since the reverse event r1 designates the Limit of the event e1, the deadline of the event e1 is corrected so that the Limit thereof is 96 which is the same as that of the reverse event r1.

From the state ES101, events are processed in ascending order of Limits. First, the event e5 is processed. The event e5 is sent by the node A to become an event directed from the node A to the node B and the new Limit thereof is set to 10. In this period, the Limit of the event e1 is counted down by 10 corresponding to the elapse of time and the Limit is 86 in the state ES103.

Furthermore, from the state ES103, the event e5 having the smallest Limit is processed. When the event e5 is processed by the node B, a new event E100 directed from the node B to the node O is generated in state ES104. The Limit of the new event E100 is 10. The Limit of the event e1 is counted down to 6.

From the state ES104, when the event e1 having the smallest Limit is processed by the node A, a new event e2 directed from the node A to the node B is published in state ES105. The Limit of the new event e2 is 10.

In this period, the reverse event queue D2 enters into state RS103. Here, it is assumed that the event e2 has the same SID as the reverse event r2. Since the reverse event r2 designates the Limit of the event e1, the Limit of the event e2 is corrected to 8 which is the same as that of the reverse event r2 in state ES106.

Figure 30:
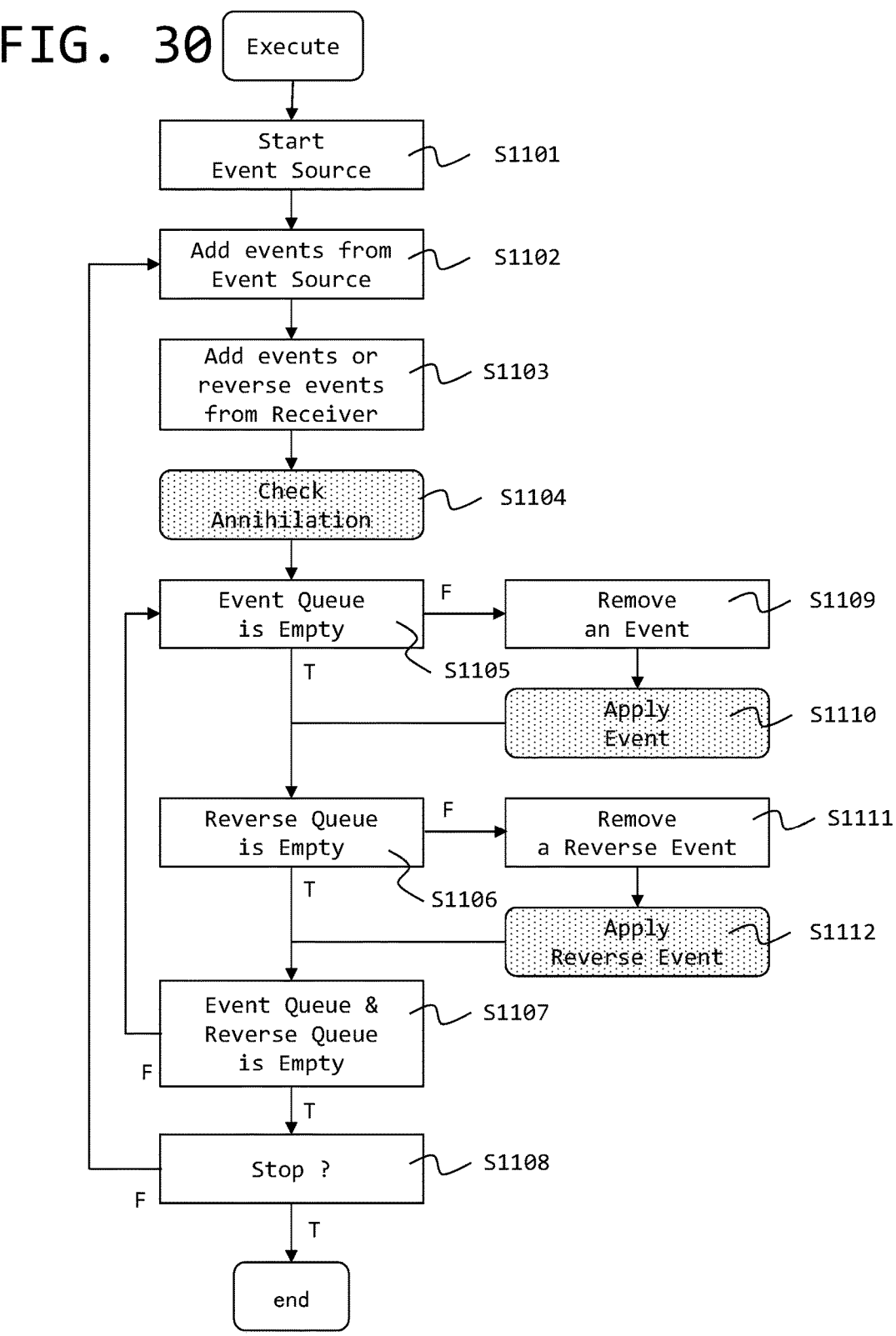
FIG. 30 is an entire flowchart of processing an event and a reverse event in the process flow.

FIG. 30 is an entire flowchart of processing an event and a reverse event in a process flow. However, a process related to a reverse event of Reserve will be described separately.

The flow executer 42 activates an event source (step S1101), adds an event from the event source to the event queue D1 (step S1102), and adds an event from the event receiver 44 to the event queue D1 or a reverse event from the reverse event receiver 45 to the reverse event queue D2 (step S1103).

Subsequently, the flow executer 42 executes a check annihilation process (step S1104). The check annihilation process is a process of organizing a reverse event and an event that match each other. The details of the check annihilation process will be described later.

Subsequently, the flow executer 42 determines whether the event queue D1 is empty (step S1105). If the event queue D1 is not empty, the flow executer 42 acquires one event from the event queue D1 (step S1109) and applies the process of the event (step S1110).

When it is determined in step S1105 that the event queue D1 is empty or after step S1110 is performed, the flow executer 42 determines whether the reverse event queue D2 is not empty (step S1106). When the reverse event queue D2 is not empty, the flow executer 42 acquires one reverse event from the reverse event queue D2 (step S1111) and applies the process of the reverse event (step S1112).

When it is determined in step S1106 that the reverse event queue D2 is empty or after step S1112 is performed, the flow executer 42 determines whether the event queue D1 and the reverse event queue D2 are empty (step S1107). If the event queue D1 and the reverse event queue D2 are empty, the flow executer 42 ends the process. If any one or both of the event queue D1 and the reverse event queue D2 is not empty, the flow executer 42 returns to step S1105.

Figure 31:
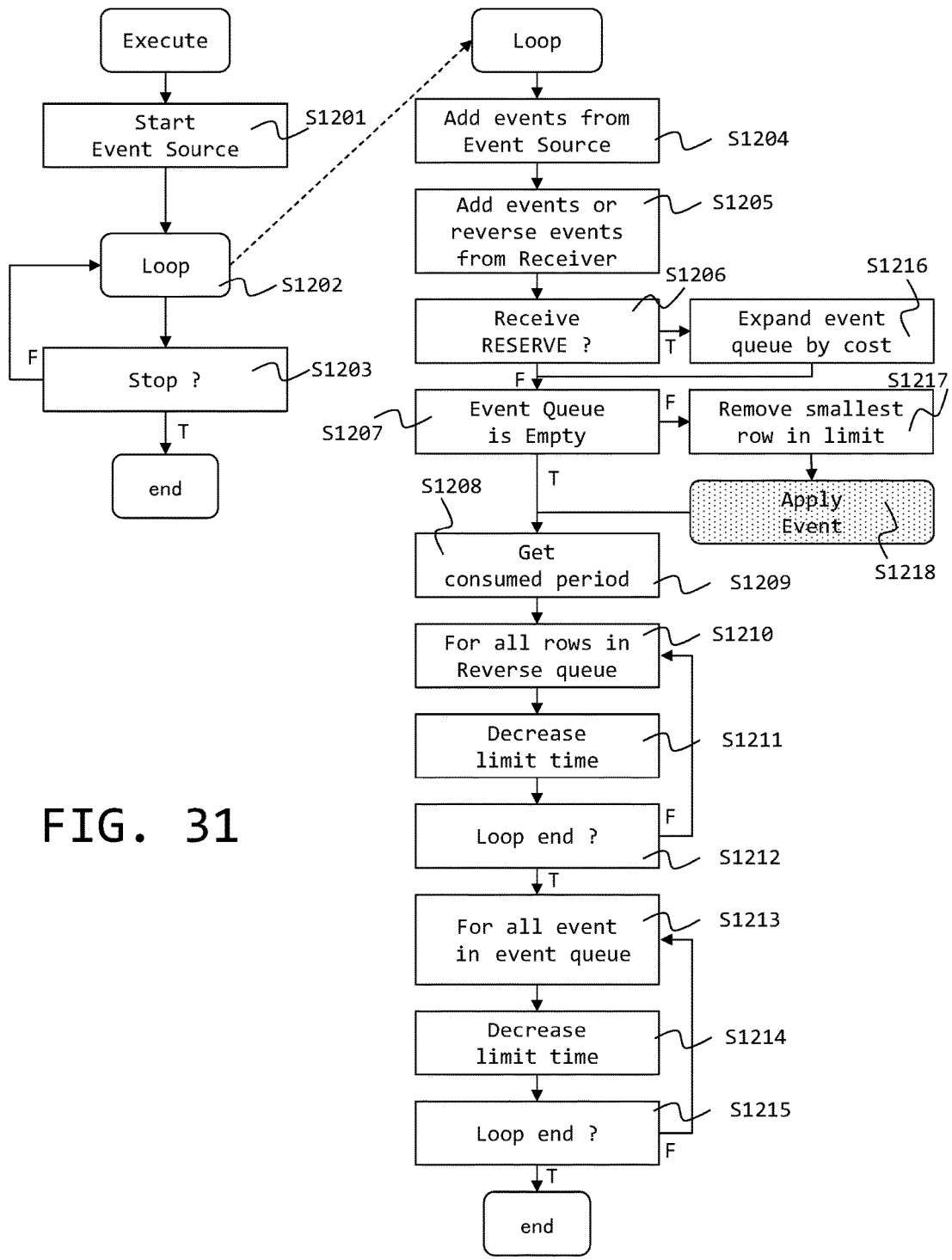
FIG. 31 is a flowchart illustrating a process for a reverse event of Reserve.

FIG. 31 is a flowchart illustrating a process related to a reverse event of Reserve. The process illustrated in FIG. 31 may be executed before or after the process illustrated in FIG. 30, for example.

The flow executer 42 activates an event source (step S1201) and then executes a loop process until a stop request is received (steps S1202 to S1203).

In the loop process, the flow executer 42 adds an event from an event source to the event queue D1 (step S1204) and adds an event from the event receiver 44 to the event queue D1 or adds a reverse event from the reverse event receiver 45 to the reverse event queue D2 (step S1205).

Subsequently, the flow executer 42 determines whether a reverse event of Reserve is received (step S1206). When a reverse event of Reserve is received, the flow executer 42 expands the reverse event on the basis of a cost as described in FIG. 28 (step S1216).

When it is determined in step S1206 that the reverse event of Reserve is not received or after step S1217 is performed, the flow executer 42 determines whether the event queue D1 is empty (step S1207). If the event queue D1 is not empty, an event on a row having the smallest Limit is extracted from the event queue D1 (step S1217), and the process of the event is applied (step S1218).

Subsequently, the flow executer 42 acquires the time elapsed after the previous Limit was computed (step S1208). The flow executer 42 subtracts the elapsed time acquired in step S1209 from the Limit time of all rows of the reverse event queue D2 (steps S1210 to S1212). Moreover, the flow executer 42 subtracts the elapsed time acquired in step S1209 from the Limit time of all rows of the event queue D1 (steps S1213 to S1215).

Figure 32:
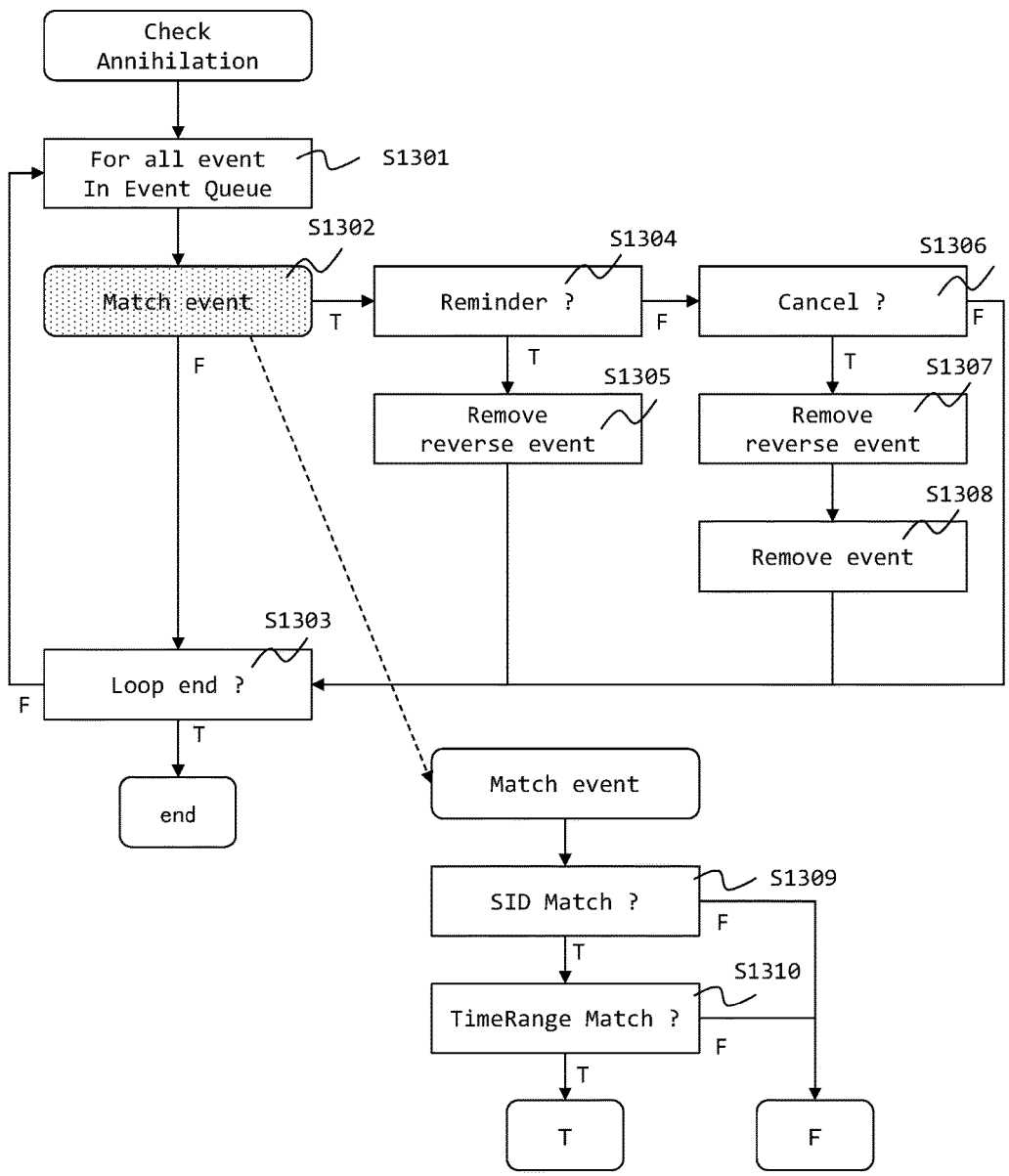
FIG. 32 is a flowchart of a check annihilation process.

FIG. 32 is a flowchart of a check annihilation process. The flow executer 42 executes a loop process to be described later sequentially for all events in the event queue D1 (steps S1301 to S1303).

In the loop process, first, the flow executer 42 performs an event match determination process (step S1302). The event match determination process is a process of determining whether a reverse event and an event match each other.

In the event match determination process, the flow executer 42 determines whether there is a reverse event of which the SID is identical to that of a target event (step S1309). When there is a reverse event of which the SID is identical to that of the event, the flow executer 42 determines whether the TimeRange of the reverse event is identical to that of the event (step S1310). If the TimeRange values are identical, it is determined that matching is achieved (T: True).

When it is determined in step S1309 that there is no reverse event of which the SID is identical to that of the event, or when it is determined in step S1310 that the TimeRange values are not identical, it is determined that matching is achieved (F: False). When matching is not achieved, the flow executer 42 determines whether the loop process is completed for all events in the event queue D1 (step S1303). The flow executer 42 ends the check annihilation process when the loop process is completed and returns to step S1301 when the loop process is not completed.

When matching is not achieved in step S1302, the flow executer 42 determines whether the reverse event is Reminder (step S1304). When the reverse event is Reminder, the flow executer 42 removes the reverse event (step S1305) and proceeds to step S1303. This is because an event that is to be activated by the reverse event is already published.

When it is determined in step S1304, the reverse event is not Reminder, the flow executer 42 determines whether the reverse event is Cancel (step S1306). When the reverse event is Cancel, the flow executer 42 removes the reverse event (step S1307) and removes the event (step S1308). The reverse event and the event cancelled thereby are removed.

After step S1305 or S1308 is performed, the flow executer 42 proceeds to step S1303.

Figure 33:
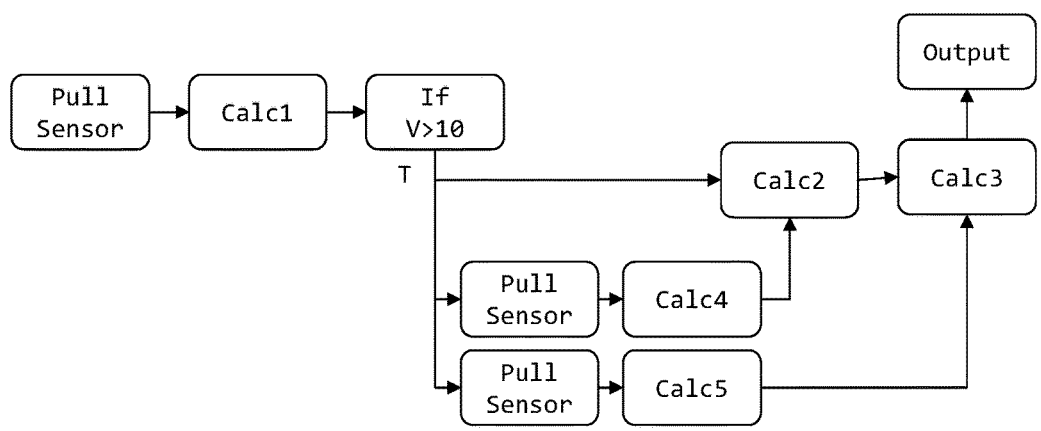
FIG. 33 is a diagram illustrating an example of a process flow which does not use a reverse event.

FIG. 33 is a diagram illustrating an example of a process flow which does not use a reverse event. FIG. 33 illustrates a command-driven process flow. When a condition of "If V>10" is satisfied, "Pull Sensor" is driven. In order to prevent a useless process from being performed by a sensor, a conditional branching operation other than a main function that a system is to perform becomes complex. As a result, the maintenance performance deteriorates. Moreover, since the process flow is adjusted for a single purpose, it is difficult to divert the process flow to another purpose.

Various process flows may be considered as a process flow which uses a reverse event according to the present embodiment.

Figure 34:
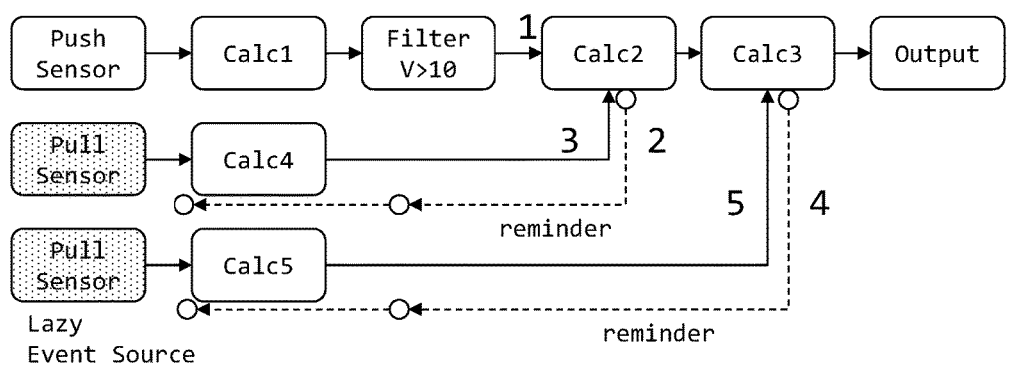
FIG. 34 is a diagram illustrating an example of a process flow which uses a reverse event of reminder.

FIG. 34 is a diagram illustrating an example of a process flow which uses a reverse event of Reminder. The "Pull Sensor" in FIG. 34 is an event source that normally does not publish an event but publishes an event only when it is requested to do so. "Calc2" is an event router that waits until all events from a plurality of input ports are received, and when all events are received, couples these events with time points and publishes the events to the downstream side. When a valid event is input from "Filter V>10", the "Calc2" sends Reminder to request "Calc4" to publish an event since an event is not input from the "Calc4". Upon receiving an event from the "Calc4", the "Calc2" publishes a valid event to the "Calc3" on the downstream side. Similarly to the "Calc2", the "Calc3" is an event router that waits until all events from a plurality of input ports are received, and when all events are received, couples these events with time points and publishes the events to the downstream side. When a valid event is input from the "Calc2", the "Calc3" sends Reminder to request "Calc5" to publish an event since an event is not input from the "Calc5". Upon receiving an event from the "Calc5", the "Calc3" publishes a valid event to "Output" on the downstream side.

As described above, when a condition of "Filter V>10" is satisfied, a reverse event of Reminder is sent from the "Calc2". The upstream-side "Pull Sensor" and "Calc4" which have stopped publishing an event receive Reminder and starts publishing an event. Moreover, when a condition of "Filter V>10" is satisfied, a reverse event of Reminder is sent from the "Calc3". The downstream-side "Pull Sensor" and "Calc4" which have stopped publishing an event receive Reminder and starts publishing an event. If in many cases the event from the "Calc1" does not satisfy the condition of "Filter V>10", it is possible to effectively reduce useless processes of the "Calc4" and "Calc5".

For example, a sensor near a sensor in which an abnormality is discovered may be asked to publish an event only when an abnormality is discovered in measurement values from all sensors.

For example, it is assumed that 54 bolts are used in the blades of a windmill of wind power generation facility, and sensors are provided so as to measure the states of the respective bolts. A process flow that calculates stress for only four bolts near a bolt in which an abnormality is discovered when an abnormality is discovered in the measurement values of sensors corresponding to any one of the bolts may be considered.

Figure 35:
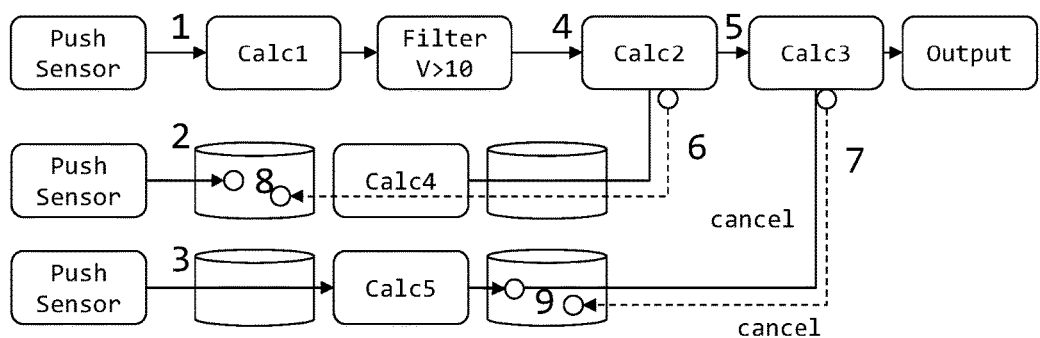
FIG. 35 is a diagram illustrating an example of a process flow which uses a reverse event of Cancel.

FIG. 35 is a diagram illustrating an example of a process flow which uses a reverse event of Cancel.

In the process flow of FIG. 34, although it is possible to eliminate a useless process, the delay time increases since publication of an event is requested after there is a need to do so. In contrast, in the process flow of FIG. 35, it is assumed that an invalid event is published to the downstream side when the condition of "Filter V>10" is not satisfied. Moreover, it is assumed that the "Calc2" publishes a reverse event of Cancel upon receiving an invalid event. Due to the reverse event of Cancel, events in the event queue are deleted and do not flow toward the downstream side. Moreover, the processes of events being processed such as computation, communication, or observation are deleted. Moreover, it is assumed that the "Calc2" publishes an invalid event to the downstream-side "Calc3" upon receiving an invalid event. Furthermore, it is assumed that the "Calc3" publishes a reverse event of Cancel upon receiving an invalid event.

When the condition "Filter V>10" is satisfied, a valid event is published to the downstream side. By doing so, since the "Calc2" does not publish a reverse event of Cancel, an event in the event queue is published and is sent to the "Calc2". Moreover, since the "Calc3" does not publish a reverse event of Cancel, an event in the event queue is published and is sent to "Output".

In this way, since an unnecessary event can be removed from the event queue, it is possible to effectively reduce a useless process on the downstream side. Moreover, since an event in the event queue starts being published when there is a need to do so, the delay time decreases.

Figure 36:
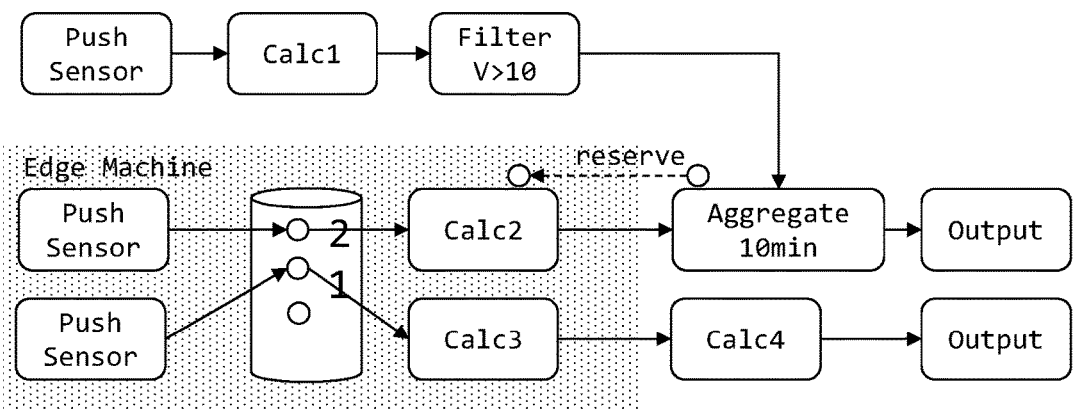
FIG. 36 is a diagram illustrating an example of a process flow which uses a reverse event of Reserve.

FIG. 36 is a diagram illustrating an example of a process flow which uses a reverse event of Reserve. For example, "Calc2" provided in "Edge Machine" near a windmill sends data of an amount of vibration of the windmill. "Aggregate 10 min" calculates statistics such as an average value using the data of the amount of vibration for 10 minutes. The "Aggregate 10 min" publishes a reverse event of Reserve and sets a processing time limit to the "Calc2" on the upstream side since it is sufficient that 10-minute data is received at a timing of calculating statistics. The "Calc2" can effectively utilize processing resources in such a way as to preferentially publish an event of which the time limit is approaching and delay publishing or processing of an event of which the time limit is late.

Figure 37:
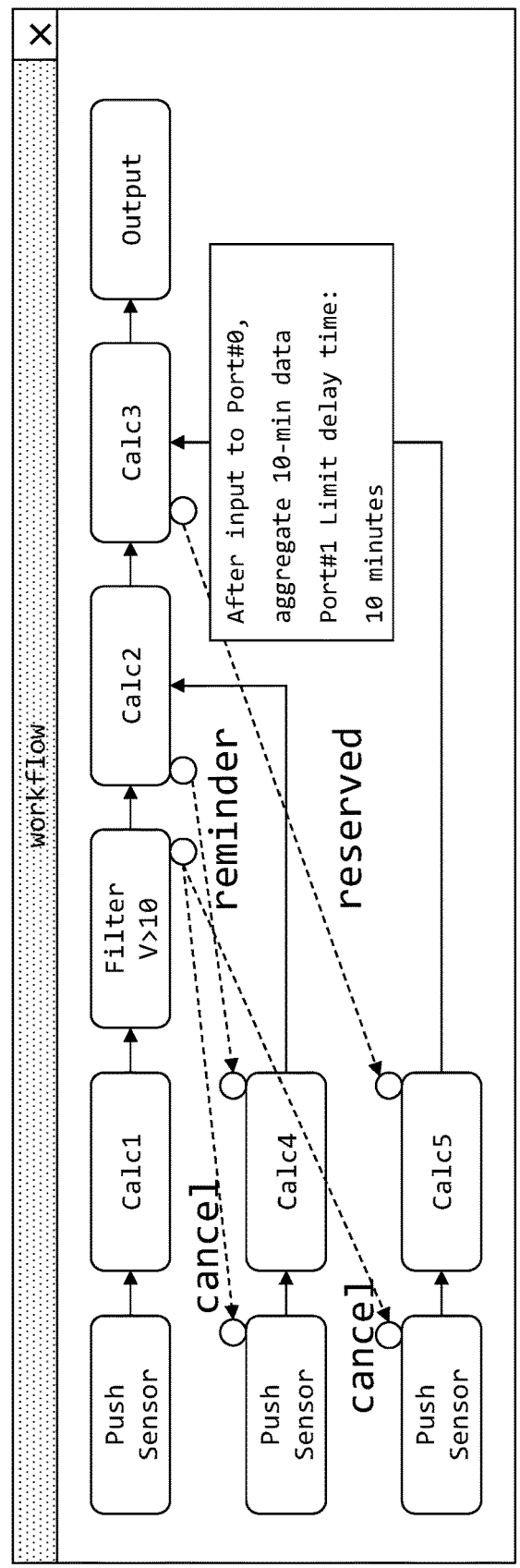
FIG. 37 is a diagram illustrating an example of screen display when a process flow is created.

FIG. 37 is a diagram illustrating an example of screen display when a process flow is created. The flow builder (a process flow builder) 57 displays a screen in which an event and a reverse event are represented by lines that connect nodes. In this way, it is possible to assist a user in building an event flow. Moreover, the flow builder 57 displays an event and a reverse event so as to be visually distinguished. In FIG. 37, an event is indicated by a solid-line arrow and a reverse event is indicated by a broken-line arrow. However, a visual distinction method is not limited to this, and other methods such as distinction based on a color or a line width may be used. Due to this, the user can easily build an event flow.

The above-described embodiment of the present invention is an example for describing the present invention, and the scope of the present invention is not limited to the embodiment only. An ordinary person in the art can implement the present invention in various other aspects without departing from the spirit of the present invention.

What is claimed is:

1. An event flow system connecting nodes, for which processes are defined, from an upstream side to a downstream side by an event which is generated due to a certain process and is used by another process to realize a process flow, the event flow system comprising:
at least a memory and a processor;
a process flow builder configured to build a process flow via a flow table using a plurality of nodes, one or more events, and a reverse event that sends a predetermined request, from a downstream node to an upstream node disposed further toward an upstream side than the downstream node;
wherein the process flow builder receives information for changing the flow table by any one of adding at least one node, deleting at least one node, adding at least one link, deleting at least one link or updating a node parameter,
wherein a link is a connection between at least two nodes that indicates the event or the reverse event,
wherein when the process flow builder deletes at least one node from the flow table, the process flow builder searches for related nodes to the at least one deleted node and deletes the related nodes,
wherein when the process flow builder adds at least one link to the flow table, the process flow builder adds destination information and source information for the at least one added link, and
wherein when the process flow builder deletes at least one link to the flow table, the process flow builder deletes destination information and source information for the at least one deleted link; and
a process flow executer configured to execute a process, stored on the flow table, defined for each of the plurality of nodes according to the event and the reverse event.

2. The event flow system according to claim 1, wherein the reverse event sends a request related to activation or stopping of a predetermined process, from the downstream node to the upstream node.

3. The event flow system according to claim 2, wherein the reverse event sends a request related to activation or stopping of publication of an event by the upstream node.

4. The event flow system according to claim 3, wherein the reverse event is a message that requests activation of publication of an event.

5. The event flow system according to claim 3, wherein the reverse event is a message that requests deletion of an event which is generated by the upstream node and is stored in a queue.

6. The event flow system according to claim 3, wherein the reverse event is a message that sets a deadline time of publication of an event by the upstream node.

7. The event flow system according to claim 1, wherein the process flow builder displays a screen that represents the event and the reverse event by using lines that connects the nodes.

8. The event flow system according to claim 7, wherein the process flow builder displays the event and the reverse event so as to be visually distinguished.

9. An event flow control method in an event flow system connecting nodes, for which processes are defined, from an upstream side to a downstream side by an event which is generated due to a certain process and is used by another process to realize a process flow, the event flow control method comprising:

building a process flow via a flow table using a plurality of nodes, one or more events, and a reverse event that sends a predetermined request, from a downstream node to an upstream node disposed further toward an upstream side than the downstream node;

wherein receiving information for changing the flow table by any one of adding at least one node, deleting at least one node, adding at least one link, deleting at least one link or updating a node parameter, wherein a link is a connection between at least two nodes that indicates the event or the reverse event, wherein when deleting at least one node from the flow table, related nodes to the at least one deleted node are searched for and deleted, wherein when adding at least one link to the flow table, destination information and source information for the at least one added link are added to the flow table, and wherein when deleting at least one link to the flow table, destination information and source information for the at least one deleted link are deleted from the flow table; and executing a process, stored on the flow table, defined for each of the plurality of nodes according to the event and the reverse event.

* * * * *